(12) United States Patent
Nelms et al.

(10) Patent No.: US 8,927,921 B1
(45) Date of Patent: Jan. 6, 2015

(54) SYSTEMS AND METHODS FOR COMPOSITE DOSE QUALITY ASSURANCE WITH THREE DIMENSIONAL ARRAYS

(71) Applicant: Sun Nuclear Corporation, Melbourne, FL (US)

(72) Inventors: Benjamin Nelms, Merrimac, WI (US); Jakub Kozelka, Melbourne, FL (US); William E. Simon, Melbourne, FL (US)

(73) Assignee: Sun Nuclear Corporation, Melbourne, FL (US)

( * ) Notice: Subject to any disclaimer, the term of this patent is extended or adjusted under 35 U.S.C. 154(b) by 0 days.

(21) Appl. No.: 14/044,811

(22) Filed: Oct. 2, 2013

Related U.S. Application Data

(60) Provisional application No. 61/708,916, filed on Oct. 2, 2012.

(51) Int. Cl.
*A61N 5/10* (2006.01)

(52) U.S. Cl.
CPC ....... *A61N 5/1031* (2013.01); *A61N 2005/1076* (2013.01); *A61N 5/1075* (2013.01)
USPC ...................................... 250/252.1

(58) Field of Classification Search
CPC ............... A61N 5/1048; A61N 2005/1076; A61N 5/1065; A61N 5/1075; A61N 5/10; A61B 6/583

USPC ...................................... 250/252.1
See application file for complete search history.

(56) References Cited

U.S. PATENT DOCUMENTS

| | | | | |
|---|---|---|---|---|
| 7,945,022 | B2 * | 5/2011 | Nelms et al. | 378/65 |
| 8,044,359 | B2 * | 10/2011 | Simon | 250/370.07 |
| 2006/0203967 | A1 * | 9/2006 | Nilsson | 378/207 |
| 2011/0248188 | A1 * | 10/2011 | Brusasco et al. | 250/492.1 |

* cited by examiner

*Primary Examiner* — Marcus Taningco
(74) *Attorney, Agent, or Firm* — Mintz Levin Cohn Ferris Glovsky and Popeo, P.C.

(57) ABSTRACT

A method for performing composite dose quality assurance with a three-dimensional (3D) radiation detector array includes delivering a radiation fraction to the 3D array according to a radiation treatment (RT) plan, measuring absolute dose per detector of the 3D array, per unit of time, determining a radiation source emission angle per unit of time, synchronizing the RT plan with the measured absolute doses and determined radiation source emission angles to determine an absolute time for a control point of each beam of the synchronized RT plan, converting the beams of the synchronized RT plan into a series of sub-beams, generating a 3D relative dose grid for each of the sub-beams, applying a calibration factor grid to each of the 3D relative dose grids to determine a 3D absolute dose grid for each of the sub-beams, summing the 3D absolute dose grids to generate a 3D absolute dose deposited in the 3D array, and determining a 3D dose correction grid for application to the RT plan based on the 3D absolute dose.

1 Claim, 21 Drawing Sheets

AC-PDP uses the 4D ArcCHECK measurements to generate a full volume, high-density measurement.

High-Resolution (i.e. small detectors)
Low-Density (1386 detectors)
Measurements

High-Resolution (i.e. small detectors)
High-Density (Full Volume)
Measurements

SYSTEMS AND METHODS FOR COMPOSITE DOSE QUALITY ASSURANCE WITH THREE DIMENSIONAL ARRAYS

CROSS-REFERENCE TO RELATED APPLICATION

This application claims the benefit of U.S. Provisional Application Ser. No. 61/708,916, filed on Oct. 2, 2012, the contents of which are herein incorporated by reference in their entirety.

FIELD OF THE INVENTION

The present invention relates to systems and methods for performing quality assurance on patient treatment plans for radiation therapy.

BACKGROUND

Modern radiation therapy is highly customized per patient plan and, with the advent of intensity modulated radiation therapy and intensity modulated radiation therapy (IMRT) and volume modulated arc therapy (VMAT), treatment plans can be very complex in nature. This precipitates the need for customized and stringent verification to ensure that: 1) the treatment planning system (TPS) calculates the patient dose accurately; and 2) the delivery system delivers the dose accurately. The process of dose verification of complex plans can be generally called dose quality assurance (QA), and will be referred to as "Dose QA" from this point forward. (Note that a common term in the industry is "IMRT QA"; but this is too limiting in its literal sense as not all modern plans are by definition IMRT.) Modern Dose QA purposes and methods have been well described in literature (e.g., B. E. Nelms and J. A. Simon, "A survey on planar IMRT QA analysis," J. Appl. Clin. Med. Phys. 8(3), 76-90 (2007); G. A. Ezzell et al., "IMRT commissioning: Multiple institution planning and dosimetry comparisons, a report from AAPM Task Group 119," Med. Phys. 36(11), 5359-5373 (2009); V. Feygelman, G. Zhang, C. Stevens, B. E. Nelms, "Evaluation of a new VMAT QA device, or the "X" and "O" array geometries," J Appl Clin Med Phys. 12(2), 146-168 (2011); B. E. Nelms, H. Zhen, and W. A. Tomé, "Per-beam, planar IMRT QA passing rates do not predict clinically relevant patient dose errors," Med. Phys. 38(2), 1037-1044 (2011); and H. Zhen, B. E. Nelms, and W. A. Tomé, "Moving from gamma passing rates to patient DVH-based QA metrics in pretreatment dose QA," Med. Phys. 38(10), 5477-5489 (2011)—the contents of which references are herein incorporated by reference in their entirety).

Dose QA performance must be quantified, and quantification requires metric(s) of performance. Acceptance of performance level (safety, accuracy, etc.) implies verifying vs. benchmarks and setting clear acceptance criteria. This general strategy, of course, relies on the metric(s) of performance being a good metric, i.e. a good indicator/predictor of quality. Scientifically and statistically speaking, a good performance metric will be both: a) sensitive and b) specific.

Sensitivity and specificity can be defined using results falling into one of four main categories, illustrated below. Nelms et al have clearly translated these categories in terms of Dose QA (see FIG. 1).

True Positive: "Sick" person correctly diagnosed as sick (in Dose QA: unacceptable dose correctly detected as unacceptable).

False Positive: "Healthy" person incorrectly diagnosed as sick (in Dose QA: acceptable dose incorrectly detected as unacceptable).

True Negative: "Healthy" person correctly diagnosed as healthy (in Dose QA: acceptable dose correctly detected as acceptable).

False Negative: "Sick" person incorrectly diagnosed as healthy (in Dose QA: unacceptable dose incorrectly detected as acceptable).

Sensitivity can be defined broadly as the ability to correctly detect a problem. In the case of medicine, sensitivity is the ability of a test to correctly diagnose a sick patient as sick. In Dose QA, sensitivity is the ability to correctly detect an error when there is an error of clinical relevance. Sensitivity can be quantified by the following equation:

$$\text{Sensitivity} = \frac{\text{Number of True Positives}}{[\text{Number of True Positives} + \text{Number of False Negatives}]}$$

Specificity can be defined broadly as the ability to correctly identify a negative result. In the case of medicine, specificity is the ability of a test to correctly diagnose a healthy patient as healthy. In Dose QA, specificity is the ability to correctly identify that there are no clinically relevant errors due to the calculation or delivery of the dose. Specificity can be quantified by the following equation:

$$\text{Specificity} = \frac{\text{Number of True Negatives}}{[\text{Number of True Negatives} + \text{Number of False Positives}]}$$

Typically the conventional QA metric is a "passing rate" (%) of calculated dose points vs. measured dose points, where the criteria for passing are a composite of percent difference, distance-to-agreement (DTA) (e.g., J. Van Dyk et al., "Commissioning and quality assurance of treatment planning computers," Int. J. Radiat. Oncol., Biol., Phys. 26(2), 261-273 (1993)), or a hybrid metric called the Gamma Index (D. A. Low, W. B. Harms, S. Mutic, and J. A. Purdy, "A technique for the quantitative evaluation of dose distributions," Med. Phys. 25, 656-661 (1998)—the contents of which references are herein incorporated by reference in their entirety). Both the DTA and the Gamma analyses serve to dampen the failures in high dose gradient regions.

In terms of conventional passing rate metrics, the regions of false positives and false negatives are illustrated in FIG. 1, as is what would be expected if these metrics are well correlated to clinically relevant errors, i.e. errors in dose volume histogram (DVH) results for patient dose distributions.

Conventional passing rate metrics, though used for many years in IMRT, were never proven in terms of either sensitivity or specificity. Recent studies of both per-beam planar IMRT methods (e.g., J. J. Kruse, On the insensitivity of single field planar dosimetry to IMRT inaccuracies," Med. Phys. 37(6), 2516-2524 (2010); G. Yan, C. Liu, T. A. Simon, L. C. Peng, C. Fox, and J. G. Li, "On the sensitivity of patient-specific IMRT QA to MLC positioning errors," J. Appl. Clin. Med. Phys. 10(1), 120-128 (2009)—the contents of which references are herein incorporated by reference in their entirety) and 3D composite dosimetry methods have proven the passing rates to be poor metrics in terms of both sensitivity and specificity, for all common methods. In other words, conventional methods/metrics cannot reliably detect significant errors (i.e. they lack sensitivity) nor can they reliably prove accuracy (i.e. they lack specificity). As such, there is a clear need for improved metrics that are not only reliable and useful, but also clinically possible and practical.

The potential limitations of conventional metrics (and especially the 3%/3 mm criteria for both %/DTA and Gamma passing rates) were postulated by Nelms and Simon and, in the same publication, the authors suggest that moving towards prediction of impact of errors on patient dose and DVH would be more useful and relevant. The authors summarize their point well: "The underlying limitation of today's planar IMRT QA approach is that it does not make the connection between the individual field analyses and the "big picture" of how the patient dose distribution might be affected—that is, how the plan DVHs might be degraded as a result of the combined planning and delivery imperfections. Today, the DVH is the critical tool for IMRT dose prescription and plan analysis. An estimated DVH (based on measurements) should perhaps be the new goal of IMRT QA. Although careful field-by-field analyses are now efficient and very effective at detecting differences between the measured fields and the planned fields, they do not predict the overall perturbations of the volumetric patient dose and DVH statistics. If meaningful standards for IMRT QA acceptance testing are to be derived and adopted, that connection needs to be made. Estimating DVH perturbations attributable to IMRT QA measurements would be a wise first step in trying to introduce meaningful standards to IMRT QA, because the benchmarks could be set based on more clinically relevant and intuitive endpoints."

A software product called "3DVH" (Sun Nuclear Corporation, Melbourne, Fla.) is one answer to solving the problems of Dose QA metrics. 3DVH uses the strategy and algorithm called "Planned Dose Perturbation" (PDP), which uses conventional QA data (measured vs. calculated phantom dose) to accurately estimate the impact of any/all observed errors on the 3D patient dose and DVH. In addition to providing these more useful metrics, the aim of 3DVH is to be clinically practical and cost-effective, specifically by allowing existing and ubiquitous QA devices to gather the required PDP measurement inputs. PDP is further described in U.S. Pat. No. 7,945,022, the contents of which are herein incorporated by reference in their entirety.

One method of dose QA is to deliver all treatment beams at their actual treatment geometries to a dosimetry phantom that acts as a patient surrogate. We will call this "true composite" dose QA (as opposed to "single gantry angle composite" where all IMRT beams are delivered at the same geometry to a flat QA phantom). The dose distribution measured and calculated in the true composite QA phantom will not be equal to the patient dose, of course (due to density and size differences), but there are advantages in delivering a full fraction and verifying the 3D dose, even if it is a phantom dose.

Though IMRT beams are dynamic in nature (moving multi-leaf collimator (MLC) leaves creating intensity modulation) they do not have dynamic beam geometries; rather, they have static beam angles per beam. However, recently dynamic arc therapy has become more commonplace. In arc therapy, the beam geometry (typically just the gantry angle) changes dynamically during a single treatment beam. Arc therapy with C-arm linear accelerators is often generalized as Volume Modulated Arc Therapy (VMAT), though it is sometimes called by vendor-specific commercial names such as RapidArc (Varian Medical Systems) or Smart Arc (Philips Radiation Oncology Systems). Another common method of dynamic arc therapy that delivers dose through a modulated fan beam that rotates in a helical loop around the patient is called helical tomotherapy, with a trade name Tomotherapy (Accuray).

Because of their dynamic beam geometries, arc therapies lend themselves to true composite dose QA rather than per-beam planar dose QA.

True composite dose QA dosimetry phantoms have followed, in a sense, the same evolution as per-beam planar. Namely, the industry has migrated towards electronic 3D arrays which measure dose without the need for time-consuming processing. In between the planar film-in-3D phantom era and the modern 3D electronic array era is wedged a history of using 2D electronic arrays embedded in 3D phantoms, a limited and semi-inaccurate method that remains common due to efficiency and cost-effectiveness. A summary of methods and devices used in true composite dose QA is given in Table 1.

TABLE 1

Summary of True Composite Dose QA Methods

| Method | Brief Desciption | Products | Pros | Cons |
|---|---|---|---|---|
| Film in 3D Phantom | Embed planes of film inside 3D phantoms | Many (Options for both film and phantoms) | User can customize measurement plane(s) User can choose their phantom (shape, material, etc.) High density measurements | Inefficient (film processing and analysis) Dose always in planes, not volumetric |
| 3D Gel | 3D chemical gel that acts analogous to a 3D "film" | BANG Gel | High density Volumetric | Inefficient (processing requires special equipment such as MR or laser scanning) Expensive Limited measurement accuracy |
| 2D Array in 3D Phantom | Place a 2D array (ion chamber or diode) inside a 3D phantom | MapCHECK MapCHECK2 PTW 729 Matrixx MapPhan* Octavius* MultiCube* * Phantoms | Inexpensive (use ubiquitous 2D IMRT QA devices) Efficient | Angular dependencies cause measurement errors Single dose plane, not volumetric Low detector density |

TABLE 1-continued

Summary of True Composite Dose QA Methods

| Method | Brief Desciption | Products | Pros | Cons |
|---|---|---|---|---|
| 3D Array | High resolution (small) detectors embedded in 3D volumetric phantom | Delta4 ArcCHECK | Efficient Volumetric | Limited to fixed detector arrangement Low detector density |

The ArcCHECK (AC) device has been well-described in literature (e.g., Kozelka J, Robinson J, Nelms B, Zhang G, Savitskij D, Feygelman V, "Optimizing the accuracy of a helical diode array dosimeter: a comprehensive calibration methodology coupled with a novel virtual inclinometer," Med Phys. 38(9), 5021-32 (2011)—the contents of which reference is hereby incorporated by reference in its entirety). The AC device is unique in its detector geometry, which features a cylindrical surface of diodes with a near-circular cross section of 22 facets and a helical progression of diodes along the long axis of the cylinder.

SUMMARY OF THE INVENTION

There are advantages and disadvantages of placing detectors in the phantom periphery rather than grouped in the middle of a phantom where the critical target dose and organ-at-risk (OAR) dose is typically located in clinical practice. However, the near-circular, peripheral AC detector surface offers key advantages related to symmetry for treatment beams whose geometries differ only in gantry angle. In particular, the detector geometry is well-suited as data input for Measurement Guided Dose Reconstruction (MGDR), which is an integral part of the AC-PDP algorithm. MGDR will be discussed in detail below. Accordingly, it is an object of the present invention to provide systems and methods for composite dose QA with 3D arrays.

Schematics diagrams along with important transformations are shown in FIGS. 2 and 3. These figures will help the reader clearly understand the AC detector geometry.

The term "AC-PDP" (short for ArcCHECK-based planned dose perturbation) is a general term that describes the use of data from the AC device as input into the algorithm that will predict the impact on patient dose. The output of AC-PDP is an estimated 3D patient dose, which when used in conjunction with 3D anatomy structures and images, can be directly compared to the planned (TPS calculated) patient dose using the analysis tools of 3DVH.

AC-PDP is a complex algorithm which is made up of several critical components. All components are the result of novel technological solutions that are unique to 3DVH and Sun Nuclear Corporation. These components will be discussed in detail, one-by-one, in the following sections of this document. First, however, the high-level roles and relationships of those components must be made very clear; understanding of the architecture of AC-PDP is essential to not only product development and regulatory governance, but also to marketing, sales, customer training, and customer support.

DETAILED DESCRIPTION OF PREFERRED EMBODIMENTS

Figure 1:
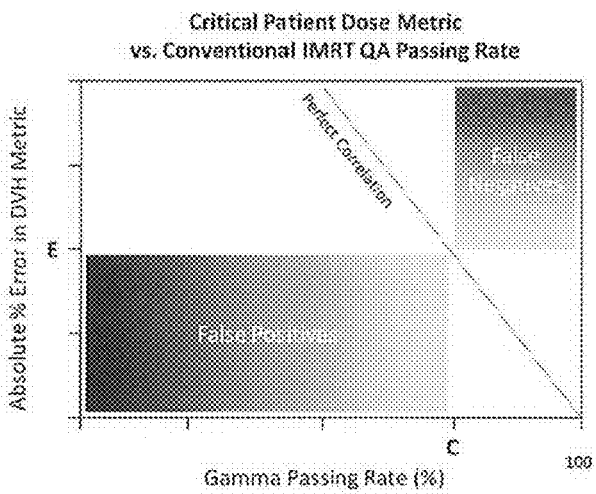
FIG. 1 illustrates false negatives and false positives in terms of conventional passing rate metrics. C represents a passing rate requirement that would ensure a DVH error of E or less.
Figure 2:
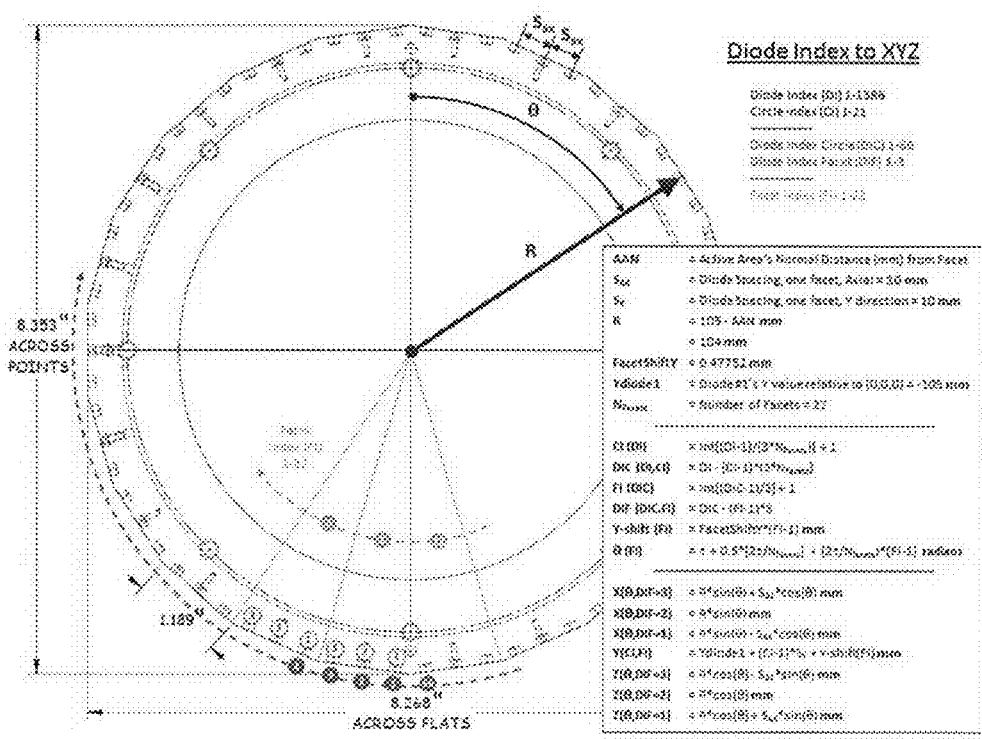
FIG. 2 is a detailed cross-section of the AC phantom and detectors along with mathematics for deriving absolute 3D (x, y, z) position from the integer diode index.
Figure 3:
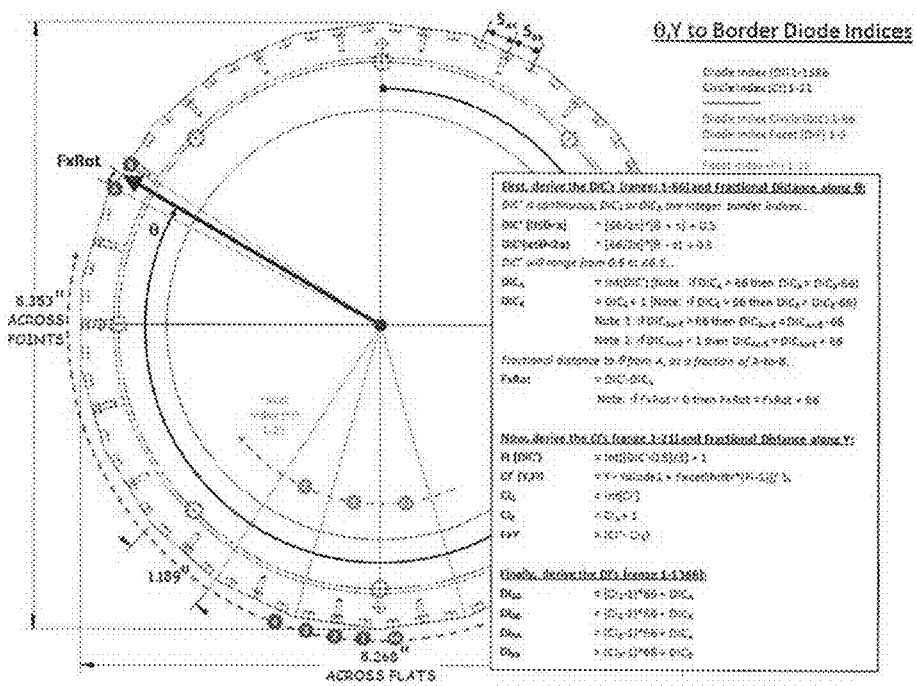
FIG. 3 is a detailed cross-section of the AC phantom and detectors along with mathematics for determining which AC diodes surround a beam ray geometry defined by an angle and a longitudinal position.
Figure 4:
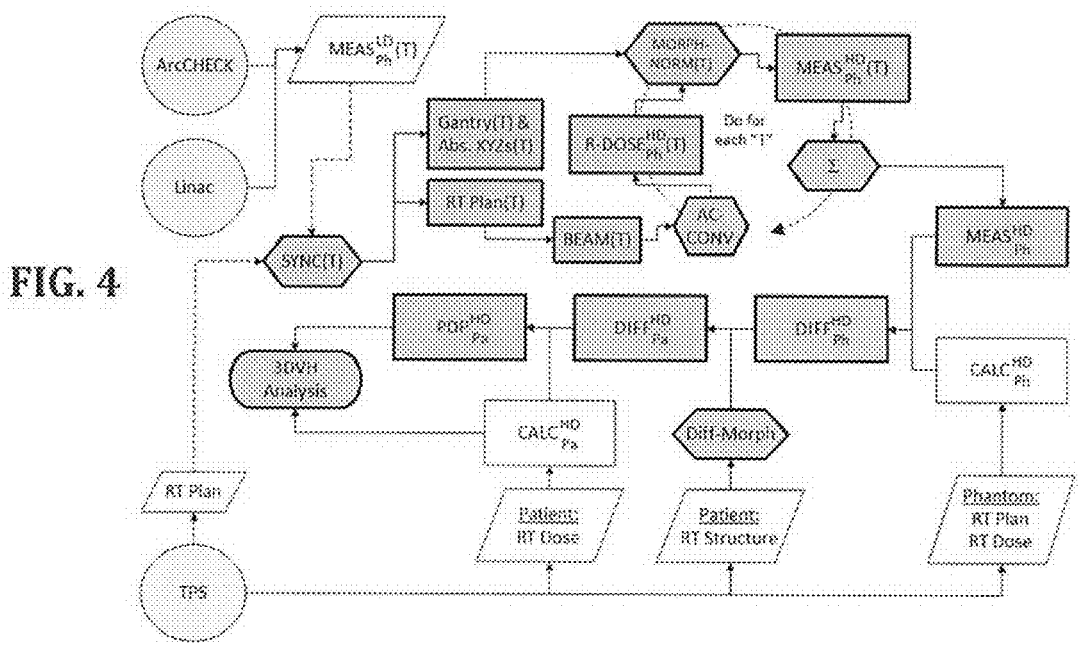
FIG. 4 is a detailed blueprint of AC-PDP components.
Figure 5:
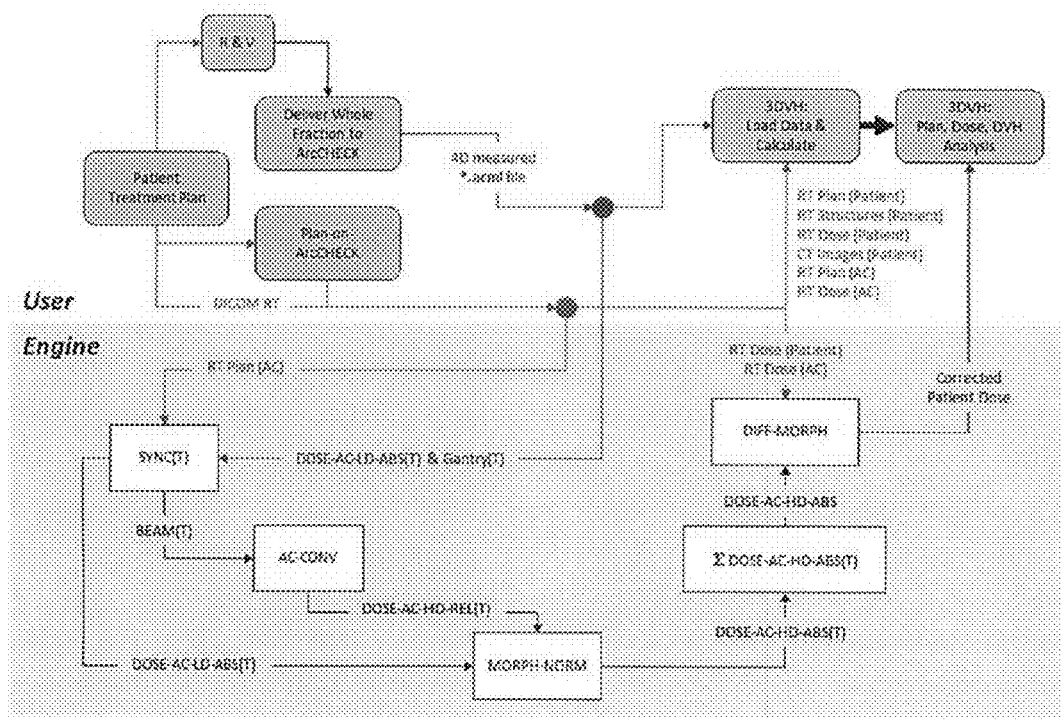
FIG. 5 is a schematic diagram of the critical components of the AC-PDP workflow ("User") and algorithm ("Engine")

FIG. 4 is a detailed blueprint of AC-PDP components, while FIG. 5 is a custom workflow figure that shows both the "user" and "engine" steps of AC-PDP. These figures will serve as guides to the component-by-component descriptions that follow.

Data inputs that are necessary to drive the AC-PDP algorithm are summarized below in Table 2.

TABLE 2

AC-PDP Data Inputs

| Data | Data Form | Data Source | Importance |
|---|---|---|---|
| Patient Plan | DICOM RT Plan | TPS | Required |
| Patient Structures | DICOM RT Structure Set | TPS | Required |
| Patient Dose | DICOM RT Dose | TPS | Required |
| Patient Axial Images | DICOM3 | TPS or Scanner | Optional |
| ArcCHECK Plan | DICOM RT Plan | TPS | Required |
| ArcCHECK Dose | DICOM RT Dose | TPS | Required |
| ArcCHECK 4D Measurement | SNC File (*.acml) | SNC Device | Required |
| AC-PDP Model | 3DVH Internal | 3DVH Internal | Required |

AC-PDP is explicitly possible because of the "4D" nature of the AC data updates. The composite AC dose (housed in the resulting composite *.txt files, and used for conventional passing rate analysis for dose at the detector positions) is, by itself, of no direct use to AC-PDP. As will become clear in the following dissection of the algorithm, the key measurement inputs required by AC-PDP are: 1) 4D measured absolute dose, i.e. absolute dose per-detector, per high-resolution unit of time, and 2) an accurate estimation of the linac gantry vs. time, often called the "Virtual Inclinometer" (VI).

The methods of acquiring the dose vs. time and VI can be found in 3DVH Release 2.0 Design History File, Algorithm Test Plan and Reports (MGDR, DIFF-MORPH, etc.), the contents of which are herein incorporated by reference in their entirety (see also, U.S. Pat. No. 8,044,359, the contents of which are also herein incorporated by reference in their entirety). The method of recording and transferring these data is via the "ArcCHECK Movie 'Lite'" file (*.acml, or ACML), a file which is rendered after the 4D raw data have been collected. The ACML houses the dose-per-diode vs. time along with the estimated gantry angle vs. time (VI). Both are updated at a default time resolution of 50 msec (though other time resolutions can be set). The low density, phantom Dose (T) and the Gantry(T) data are processed first by the "SYNC" function which is implemented generally in a class library (called a dynamically linked library, or DLL) so that it can be used by other SNC software applications.

Figure 6:
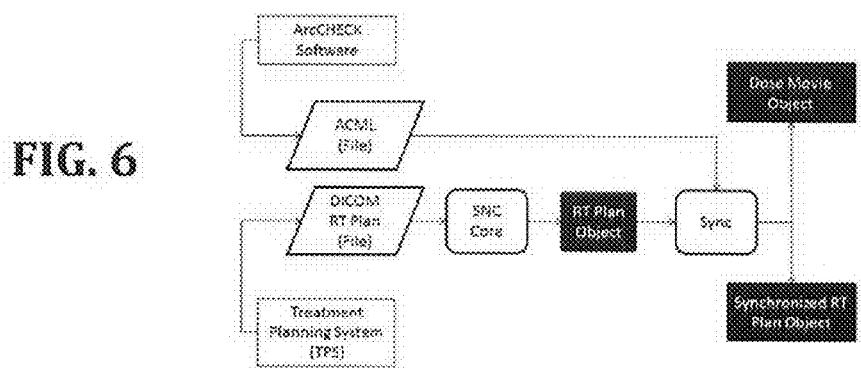
FIG. 6 is a schematic diagram showing inputs and outputs of the SYNC function.

SYNC will use AC movie data (ACML) in conjunction with the corresponding DICOM RT Plan to "synchronize" the DICOM RT Plan's Beams' Control Points to absolute, corresponding delivery times. The primary outputs of the Sync function are shown in FIG. 6 and are summarized below:

A revised RT Plan object where all the plan's beams' control points have both "Time" (seconds) and "Time-Validated" (True or False) values assigned.

A "Machine Movie" object with: 1) gantry angle vs. time, and 2) 3D dose cloud (cumulative and differential dose) vs. time for discrete XYZ points, specifically the positions of the AC diodes.

SYNC output is important to AC-PDP as it enables (i.e. is an input to): 1) Discretization of the entire RT Plan's beams into a larger set of many sub-beams, BEAM(T), that are required input for AC-CONV; and 2) MORPH-NORM—the synchronization of 3D high-density dose-to-AC relative dose calculations to the AC measured dose movie, from which select detector doses will be used to calibrate each sub-beam's high-density, relative dose grid to be absolute dose.

Figure 7:
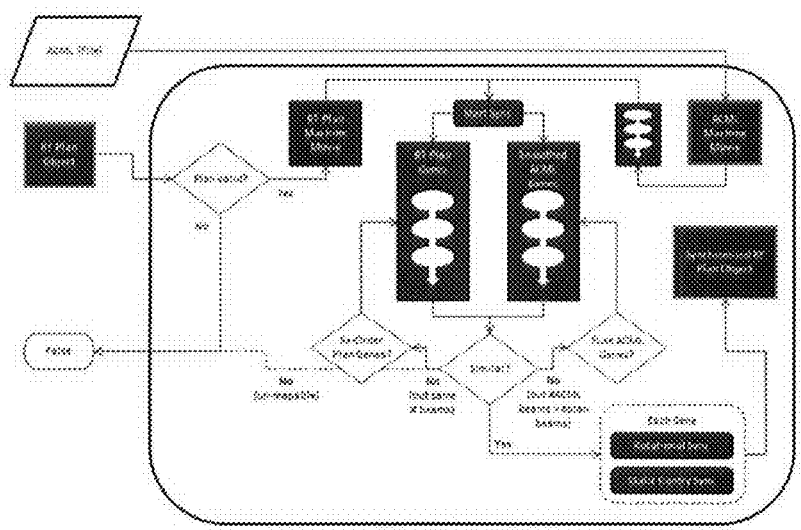
FIG. 7 is a schematic diagram of the SYNC process.

A mid-level architectural chart of how SYNC works is shown in FIG. 7. The concept of a "beam gene" is used, where a beam gene is a unique section of a delivery defined by its geometry and dynamics. The ACML is processed into beam genes, as is the RT Plan. Beam genes are matched by their genotypes, and if each delivered beam has a unique match in the RT Plan, then the RT Plan's beams' control points are assigned absolute time values based on a gantry angle-based lookup/interpolation using the VI data, i.e. gantry vs. time, and the gantry angles of the control points. It there is not a unique match between delivered and planned beam genes, then attempts are made at finding permutations of re-ordering (of plan beam genes) and fusing (of delivered beam genes) to create a match. (NOTE: Fusing of delivered beam genes is required for beams that had delivery interruptions making a single beam appear at first to be two or more beams.) Also vital to SYNC is the post-processing of the raw VI data; smoothing and interpolation algorithms are built into the SYNC function to improve the accuracy of the gantry vs. time data and to fill in missing gantry angles.

It is important to note that for static gantry beams (such as IMRT), there is no intra-beam gantry change vs. time and thus only the first and last control points can be accurately time-stamped. This is important in the discussion of subsequent steps of AC-PDP, as it places limitations on AC-PDP with static gantry modulated beams. This will be discussed more in the section "AC-CONV".

Figure 8:
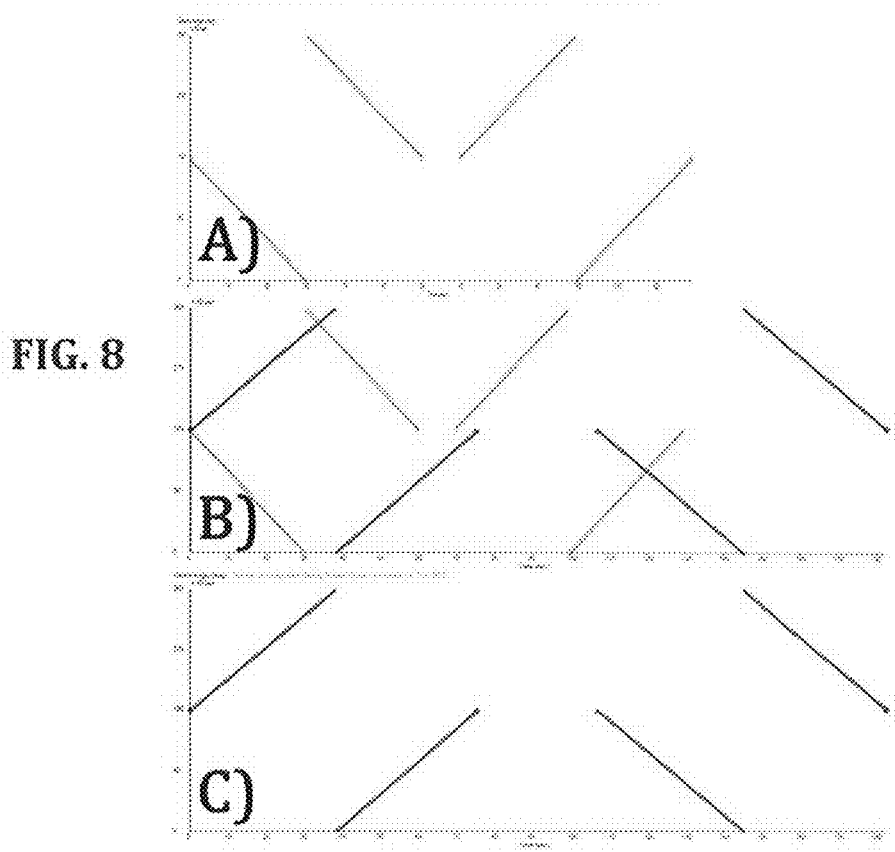
FIG. 8 is a 2-Beam VMAT plan's Gantry vs. Time illustrated using 3DVH's 4D Workspace.
Figure 9:
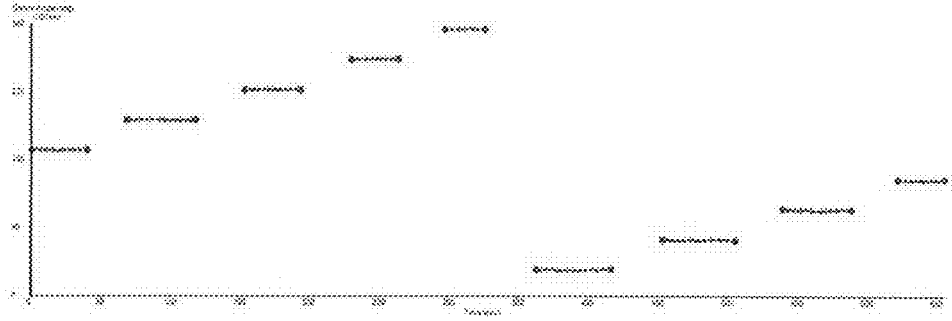
FIG. 9 is a 9-Beam IMRT plan synchronized to ACML.

Examples of the SYNC results as seen in windows of 3DVH's "4D Workspace" are shown in FIGS. 8 and 9. In FIG. 8, graph A) is RT Plan control points pre-SYNC; graph B) is Unsynchronized RT Plan loaded alongside the beam movie object derived from the ACML; and graph C) is RT Plan synchronized to the ACML. Each vertical red hash mark represents an RT Plan control point, while the blue line is plotted from the post-processed (smoothed and interpolated) gantry vs. time data from the VI.

In FIG. 9, results from a step-and-shoot IMRT plan are shown, so the number of control points (seen as vertical red hash marks) is not very dense. Note that the blue curve (ACML gantry vs. time) has many interpolated points (thin instead of thick blue line) due to dose not being delivered during the "step" portion of the step-and-shoot delivery, i.e. when there is no dose delivered, there are no data to fuel the VI calculation, but gantry angles are filled in later during SYNC post-processing.

One of the outputs of SYNC is the synchronized RT Plan, where each treatment beam's control point is assigned an absolute time that is directly related to the 4D low density measured data. Data from the synchronized RT Plan are consumed by the ArcCHECK Convolution (AC-CONV) component of AC-PDP.

The process of AC-CONV can be separated into its major steps:

1) Process the dynamic RT Plan into a series of many sub-beams that are each represented as static beams (fixed beam geometries, i.e. static gantry);
2) For each sub-beam, interpolate and process the control point data to create modulated fluence per sub-beam;
3) Create a 3D impulse function of total energy released per unit mass in the AC volume using the "TERMA+" parameters and the off-axis depth kernels as configured in the PDP model specific to the linac model and energy; and
4) Convolve, via Fast Fourier Transform (FFT), the TERMA+3D grid for each sub-beam with the 3D dose scatter depth dose kernels (also tailored to a linac model and energy) to generate a relative 3D dose grid for each of the time-resolved sub-beams.

Figure 10:
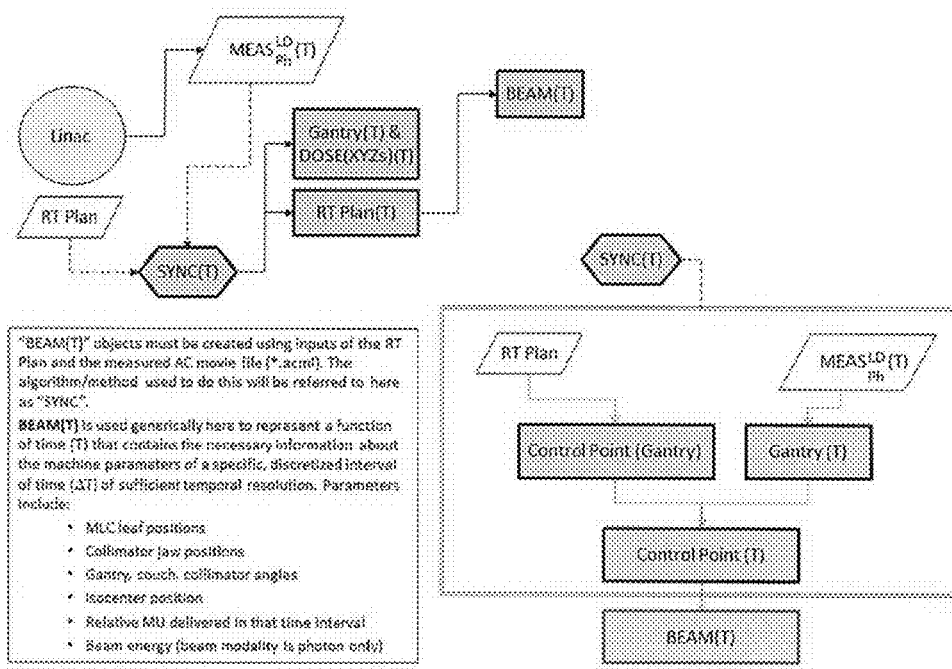
FIG. 10 is illustrates a discretization of RT Plan dynamic beams into discrete beams with static beam geometries.
Figure 11:
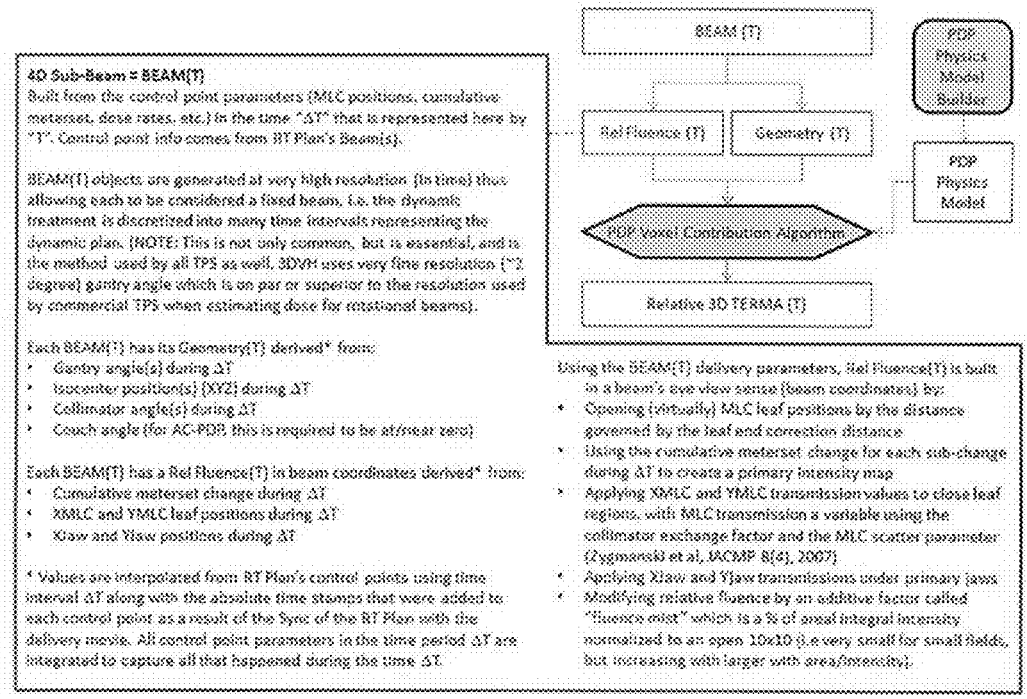
FIG. 11 illustrates details of building the per sub-beam 3D TERMA+ grid.
Figure 12:
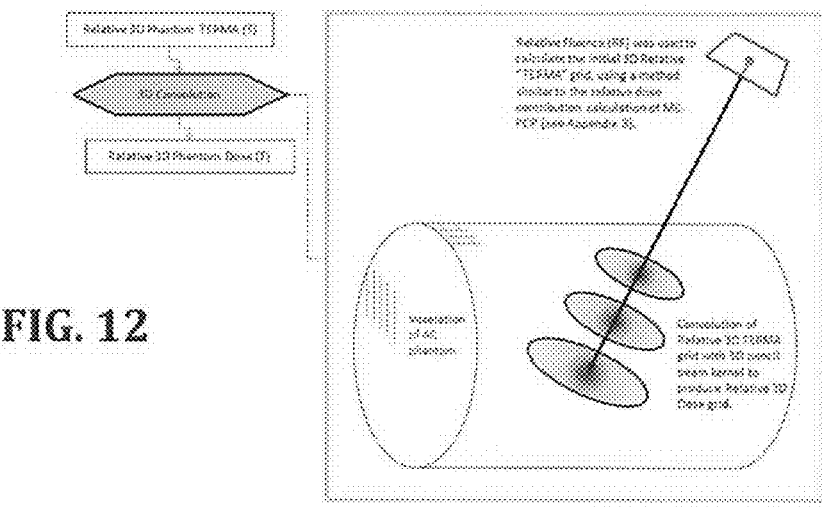
FIG. 12 illustrates details of the 3D convolution of TERMA+3D dose deposition kernels to give high-density, relative dose per sub-beam.

Step 1 is detailed in FIG. 10, Steps 2-3 in FIG. 11, and Step 4 in FIG. 12.

The TERMA+ and 3D convolution algorithms are customized per linac model and energy and are designed specifically for the plugged AC phantom, i.e. AC plugged to make a homogeneous volume of the phantom plastic. The output of AC-CONV is a high density, volumetric, relative dose grid for each time-resolved sub-beam. This output is an input to the next step of AC-PDP, called MORPH-NORM.

The discretization of the RT Plan dynamic beams into many sub-beams is set to give sub-beams that cover roughly 2 gantry degrees (sometimes slightly higher). This is similar to the discretization used by modern treatment planning systems. As mentioned earlier, IMRT plans already have multiple (usually between four and 200) dynamic MLC control points but those dynamics change while the beam geometry is static. Thus, gantry vs. time data intra-beam cannot be used to synchronize all the control points to absolute time, and in fact only the beam start and end can be time-stamped. Thus, the AC-CONV sub-beams reduce to the RT Plan beams and the time resolved calibration to absolute measurements (MORPH-NORM) is limited to very large time intervals.

The high-density, 3D relative dose grids per sub-beam are transformed into absolute dose as the next stage of AC-PDP. This is done via the component called "MORPH-NORM" which stands for the morphing dose normalization that converts relative dose values to absolute dose using the 4D diode measurements as real-time calibration (normalization) data.

Figure 13:
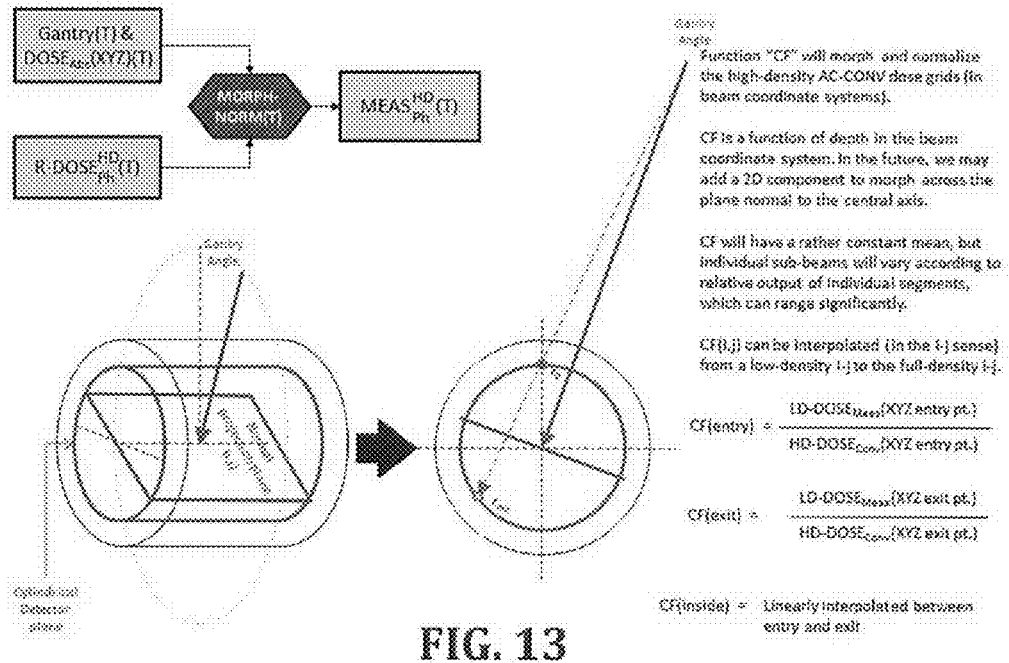
FIG. 13 is a schematic of MORPH-NORM, which uses a 3D morphing per sub-beam to normalize a relative dose grid into an absolute dose grid.
Figure 14:
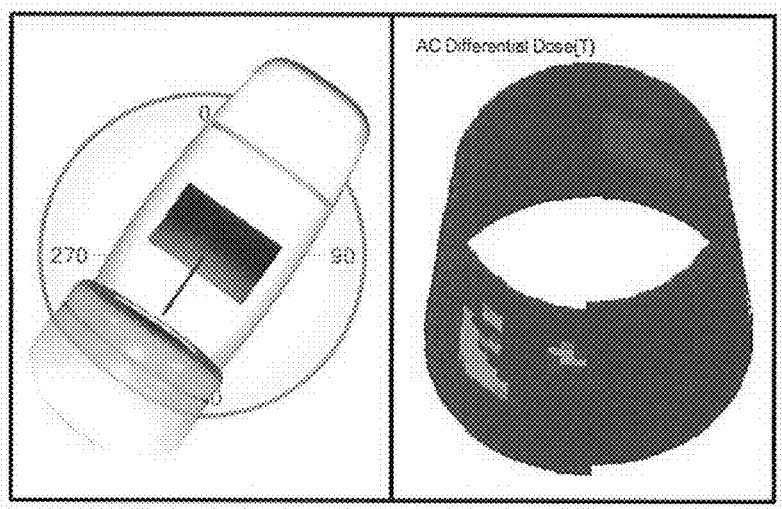
FIG. 14 illustrates a sub-beam from gantry angle~215 degrees (IEC) and its entry and exit absolute dose projections.
Figure 15:
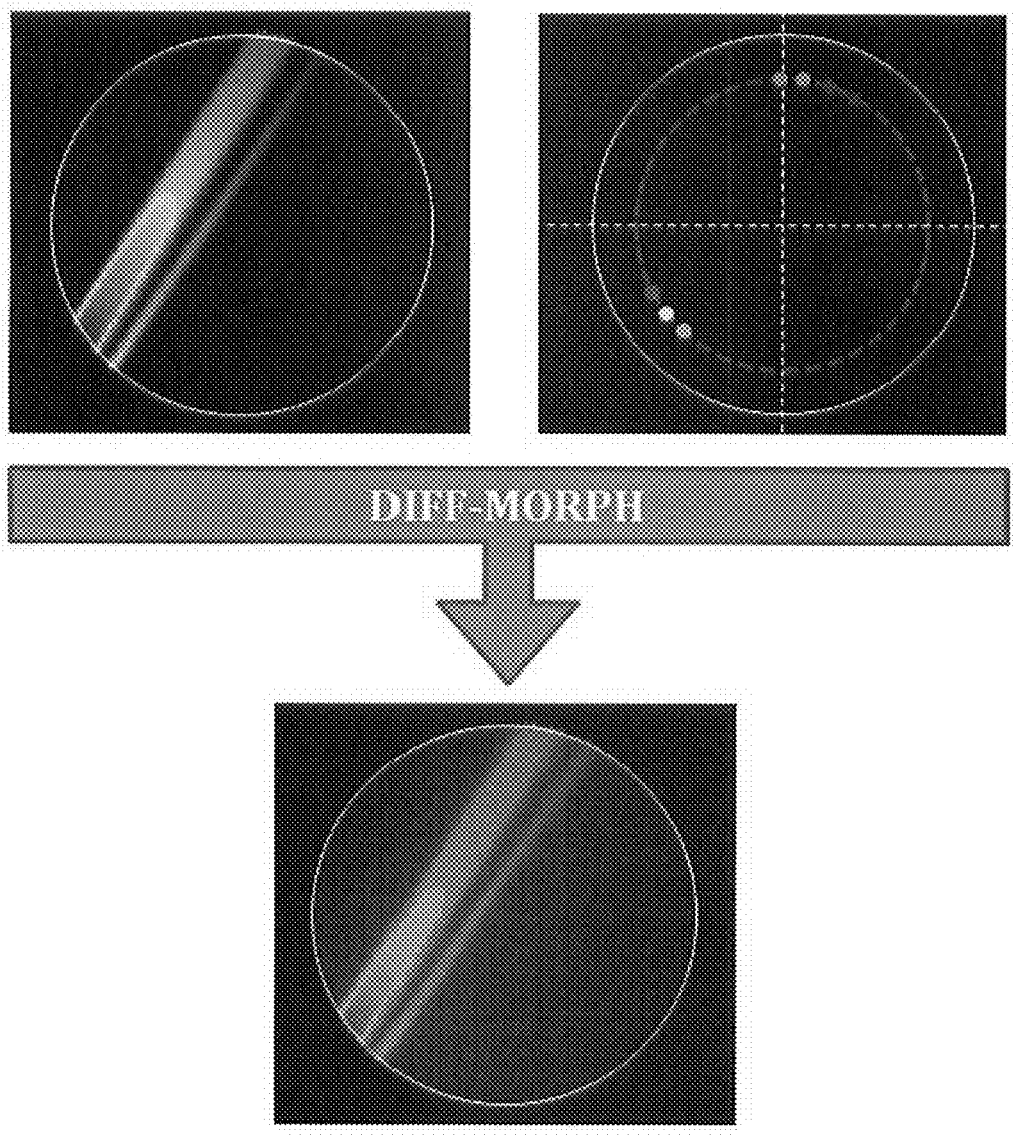
FIG. 15 illustrates the sub-beam from FIG. 14 after processing with MORPH-NORM.

MORPH-NORM is illustrated in FIGS. 13 through 15. MORPH-NORM applies a 3D calibration factor grid to each sub-beam's high-density, relative dose. The 3D calibration grid is built from relevant entry and exit diodes' absolute doses per sub-beam. The resulting output is a high-density, absolute dose grid (lower) for the sub-beam. Here, "relevant" in a mathematic sense is defined by the following requirements:

1) The diode's dose is above a qualifying threshold (there is a different threshold for entry and exit surfaces). Default AC-PDP settings use a threshold of 80% of the respective surface's maximum diode dose.
2) The diode is not on a high gradient. The gradient of a diode is quantified in a beam's-eye-view (BEV) sense from the sub-beam's relative fluence map. Default settings of AC-PDP will consider a diode on a high gradient if the relative fluence changes by 10% over a 4 mm radius for that BEV projected to 100 cm. High gradient diodes, even if the diode dose meets the threshold criterion, are not used in the MORPH-NORM function, because these diodes are too sensitive with respect to various geometric considerations such as VI errors, diode placement vs. nominal, and accuracy of AC setup.

A best-fit entry calibration factor and exit calibration factor are found for each surface, and all of the sub-beam's beamlets (rays) are projected from curved surface to curved surface, with calibration factors in between being interpolated based on the entry and exit values. The nature of the entry and exit being allowed to have different calibration factors is the genesis of the "morph" component of MORPH-NORM. If a single calibration factor was used, it would be only a simple normalization (SIMPLE-NORM), i.e. a scaling of the dose grid and not a morphing. (NOTE: SIMPLE-NORM AC-PDP can be done while in service mode, if useful for diagnostic purposes. Also, the can be a further option called "ÜBER-NORM" which allows morphing BEV ray in addition to morphing with depth, but this would preferably be applied only to fixed gantry IMRT beams at first due to its impact on the speed of calculation.)

If for any sub-beam there are not diodes at the entry or exit surface qualifying to guide MORPH-NORM, then a nominal calibration factor will be used. This only occurs for very small volume (small segment) sub-beams and the effect of not having qualifying diodes is minimal due to a relatively small impact on the overall dose.

AC-CONV and MORPH-NORM are performed for each and every discrete sub-beam(T) that are used to model the entire treatment fraction. The next stage is to complete the high-density virtual measurement in the AC phantom by summing all the sub-beams dose grids and doing some post-processing. In FIG. 15, the high-density, relative dose grid calculated by AC-CONV (upper left) and the low-density absolute dose measured by AC (upper right) are inputs into the MORPH-NORM function.

Figure 16:
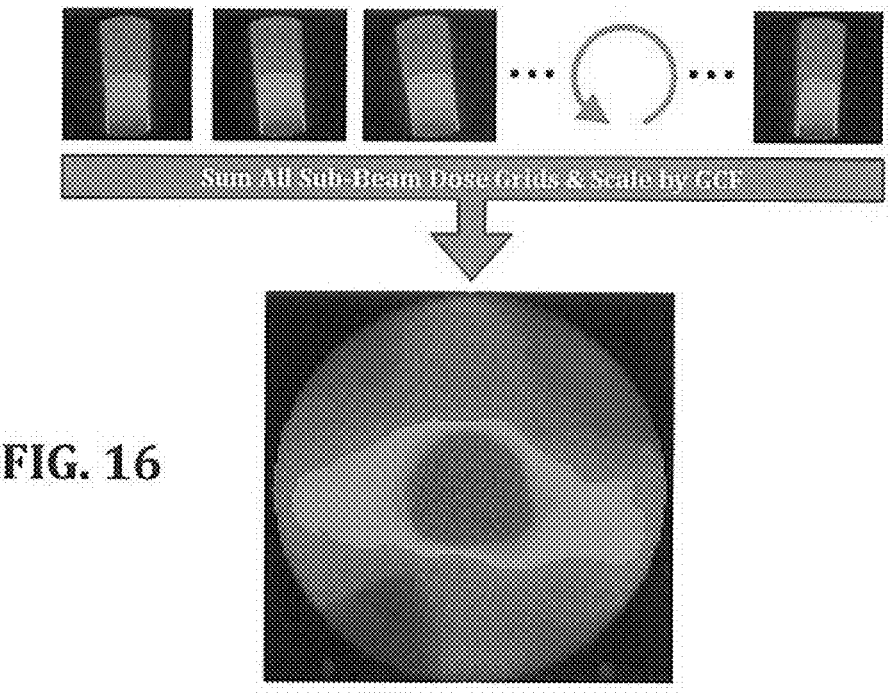
FIG. 16 illustrates sub-beam(T) dose grids being summed and the sum being scaled by the GCF to give the resulting full-volume virtual measurement.

The next step in AC-PDP is to generate a full-volume, high-density absolute dose grid in the AC phantom using all the sub-beam dose grids. This result could be thought of as a "virtual measurement" or, because it is a full volumetric dose, a "virtual BANG gel". The dose grids from all sub-beams are summed, and a final processing step is performed which scales the dose by a global calibration factor (GCF) that best fits the virtual measurement to the composite (cumulative) doses per diode position. The "best fit" is defined by minimizing the cumulative dose differences for all diode doses above 30% of the max diode dose, and the GCF will only be applied if at least 12 diodes meet that threshold (otherwise, the GCF is fixed at 1.00). The GCF should always be, and in most cases is, very close to 1.00. In some rare cases (usually if the target volume is very large or very small) it may range from 0.98 to 1.02; any GCF outside this range could indicate either bad input data, improperly assigned PDP model, dose measurement/calibration error, or some other issue. FIG. 16 illustrates the summing of sub-beam dose grids and post-processing with GCF to generate the composite virtual measurement. It is important to note that AC-PDP only reconstructs dose inside the detector surface, and all dose values outside of that cylinder are set equal to the TPS dose. In the case of FIG. 16, the GCF was 0.993 which is close to 1.00, as is expected. Note that in this case, the reconstructed dose is less than the TPS dose, as evidenced by the visible discontinuity at the edges of the "reconstruction volume"; this is because AC-PDP does not estimate dose outside of the reconstruction volume (detector surface). The reconstructed dose was accurate however, as the AC measurements were actually 3-5% lower (vs. TPS) for this case.

Figure 17:
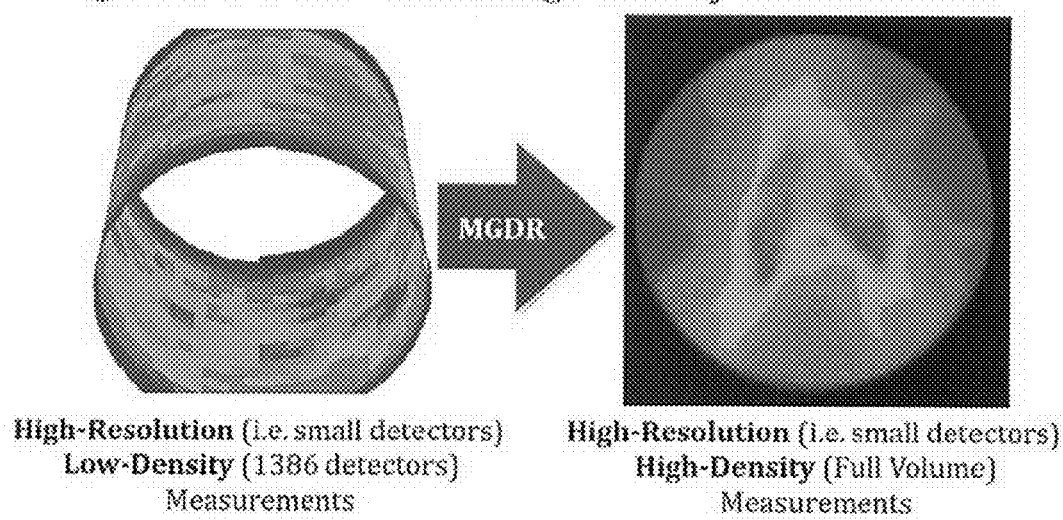
FIG. 17 illustrates the transition from 4D ArcCHECK measurements to a fully volume, high-density measurement.

At this point, the entirety of the AC-PDP algorithm has served to produce a high-density, full-volume, 3D absolute dose in the AC phantom. The required steps are inherently 4D, requiring time-resolved VI and absolute dose data, along with the time course of high-density relative dose calculations. The generation of a full-volume, high-density absolute dose phantom measurement can be generally described as "Measurement-Guided Dose Reconstruction" (MGDR)—see FIG. 17. MGDR is the primary engine behind AC-PDP algorithm. MGDR is proven to be extremely accurate.

Once AC-PDP has generated an accurate MGDR estimate, the hard work of AC-PDP has been done. However, the depth of knowledge and intuitive analysis that can be gained from the full-volume, high-density phantom virtual measurement can be truly realized if the effects (differences between MGDR and TPS dose-to-phantom) can be used to estimate the impact on patient dose.

Figure 18:
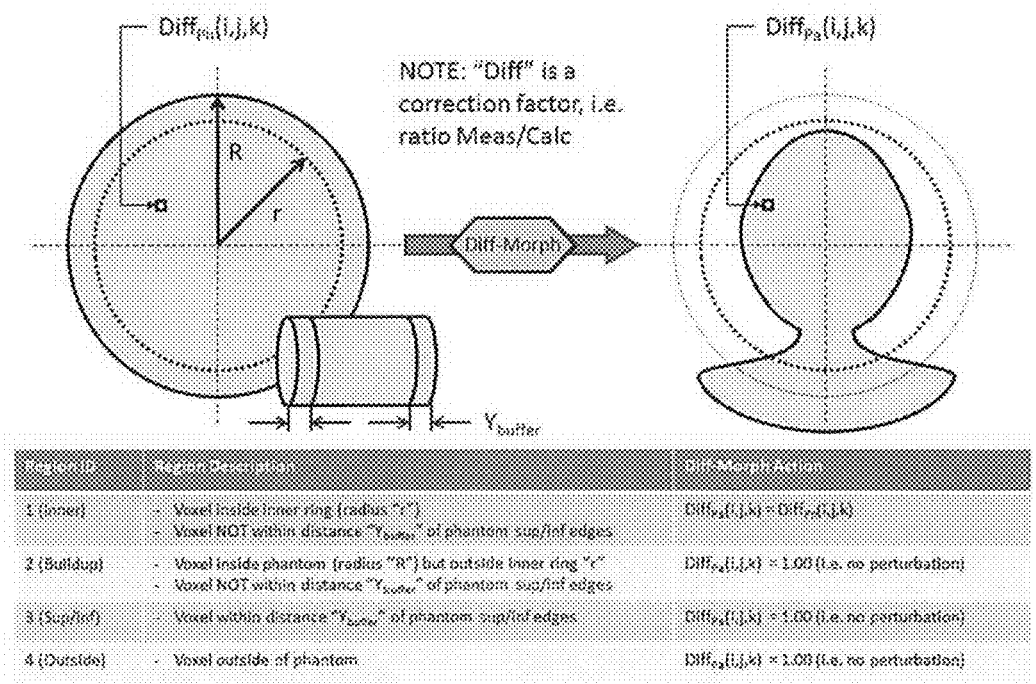
FIG. 18 is an illustration of DIFF-MORPH.
Figure 19:
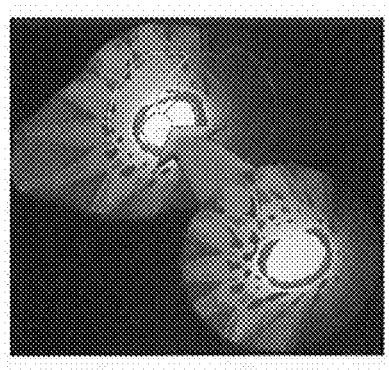
FIG. 19 is a simple schematic giving an intuitive feel for DIFF-MORPH.

In MC-PDP, the perturbation (correction) of TPS calculated dose was voxel-by-voxel and beam-by-beam, using correction factors per beamlet garnered from dose planes normal to the CAX. With dynamic beam geometries and 3D dosimetry, we do not have implicit "pairs" of measurements and calculations per beam geometry, so we cannot use the MC- PDP strategy to estimate the impact on patient dose. However, as it turns out, if an absolute dose difference is known accurately in a 3D phantom, the errors translate very closely to those in a 3D patient, despite the patient size, shape, and density being different than the phantom. Thus, a 3D dose correction grid based on the phantom can be directly applied to the TPS patient dose, using a process called DIFF-MORPH, meaning to morph the patient dose based on the phantom dose differences. DIFF-MORPH in AC-PDP only perturbs (corrects) dose inside the reconstruction cylinder defined by the AC detector surface, but this volume most often contains the entirety of the targets and OARs. For target and/or OAR volumes falling outside the size of the AC detector cylinder, AC-PDP will not change the dose from the TPS dose. DIFF-MORPH is described in FIGS. 18 and 19.

The simplicity of DIFF-MORPH is striking and can leave a physicist skeptical. However, the DIFF-MORPH strategy (for predicting impact on patient dose and DVH) is proven accurate over various patient sizes, shapes, and densities.

A failure mode analysis of AC-PDP reveals that the AC-PDP strategy will fail if MGDR results (phantom dose) exhibit differences that are either inaccurate or are not manifest in the patient dose. This could be due to the following conditions, which should therefore be avoided:

User sets the AC phantom without the isocenter located at the phantom center;

User acquires dose with the AC phantom hollow (i.e. unplugged) or uses the wrong plug;

ACML virtual inclinometer has errors, causing inaccurate discretization of sub-beams from RT Plan control points, which would impact the AC-CONV relationship to MORPH-NORM diode doses;

AC-CONV model gives inaccurate 3D relative AC dose for sub-beams due to incorrectly assigned PDP Model for the treatment machine/energy;

ArcCHECK is mis-calibrated, resulting in erroneous absolute doses that are used in MORPH-NORM;

PDP model parameters are not optimal;

User's virtual phantom model is incorrectly defined in the TPS, resulting in errors in the TPS AC dose that will impact DIFF-MORPH;

TPS AC dose is not properly aligned in 3DVH, resulting in data shifts that will impact DIFF-MORPH;

TPS has dose errors that manifest in PMMA/acrylic phantom geometry but not in a patient.

Figure 20:
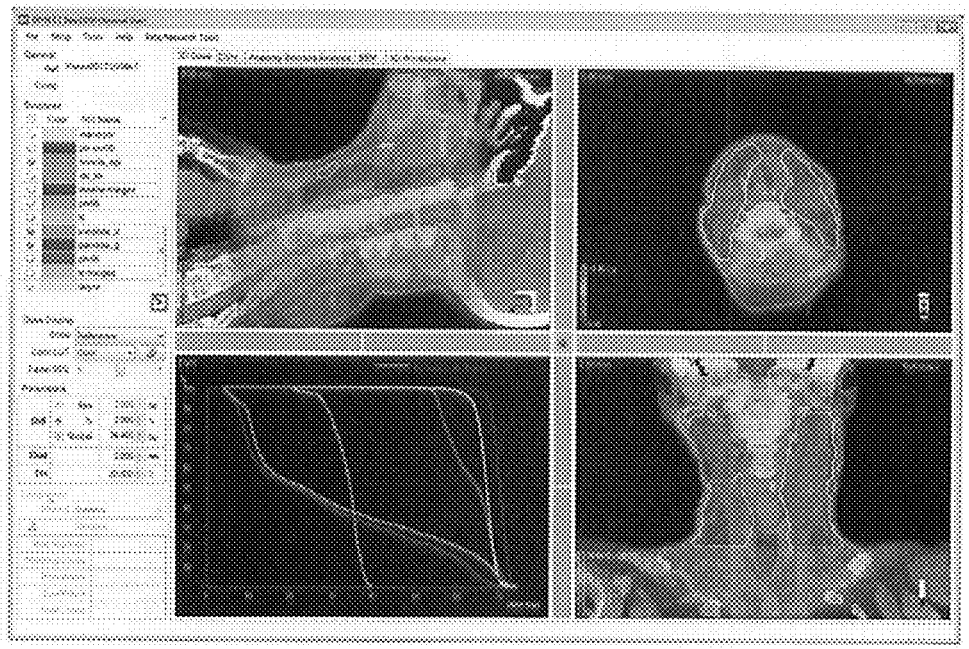
FIGS. 20-30 illustrate major workflow steps of AC-PDP.
Figure 21:
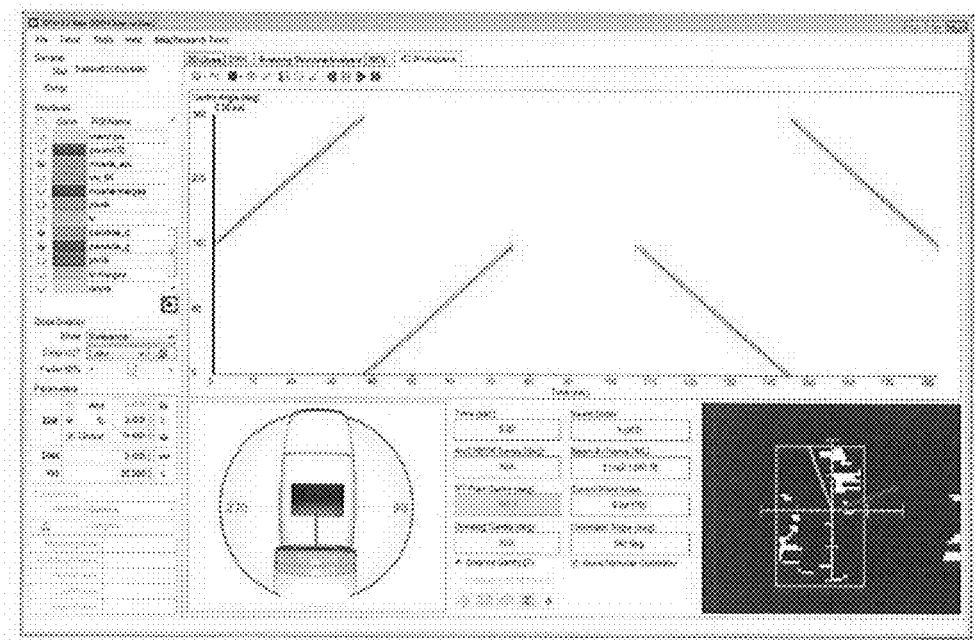

Now that the technical components of the AC-PDP engine are understood, it is useful to highlight some of the major user workflow steps to recognize at which point the AC-PDP components are taking, or have taken, place. These are summarized in FIGS. 20 through 30. In FIG. 20, the DICOM RT plan, structure set, and dose are loaded as the reference dose (shown in the 3DVH interface). FIG. 21 illustrates a window showing the unsynchronized RT Plan, before loading of the ACML file and subsequent SYNC of the plan's control points.

Figure 22:
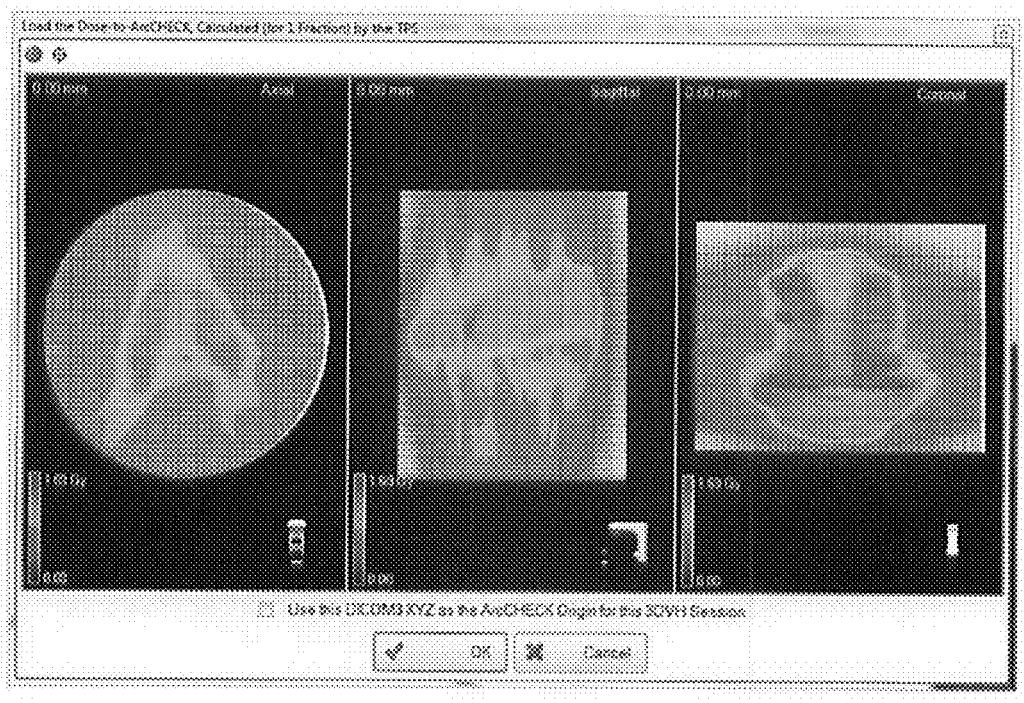
Figure 23:
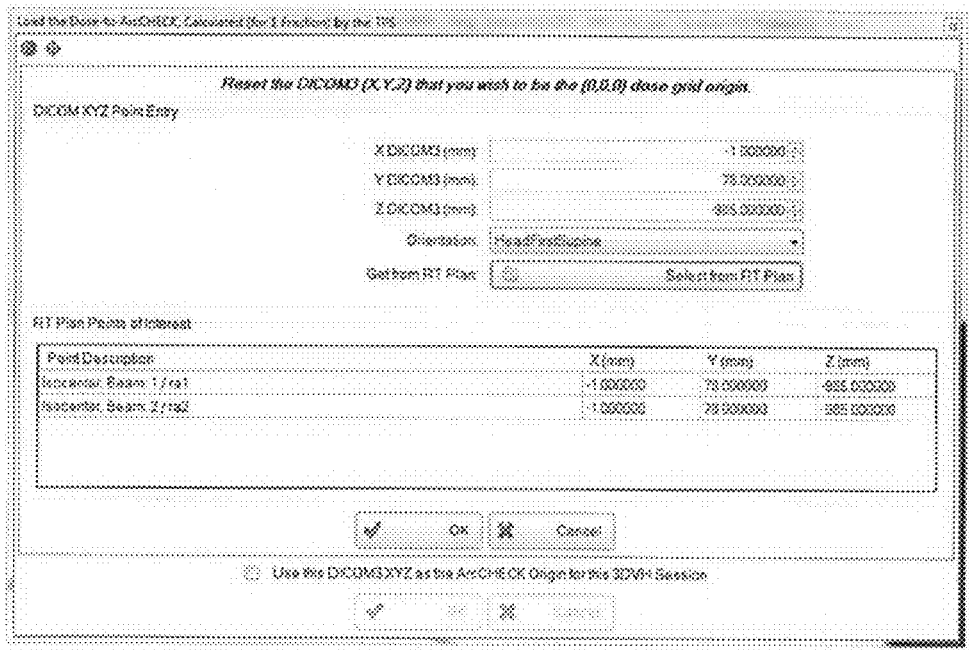
Figure 24:
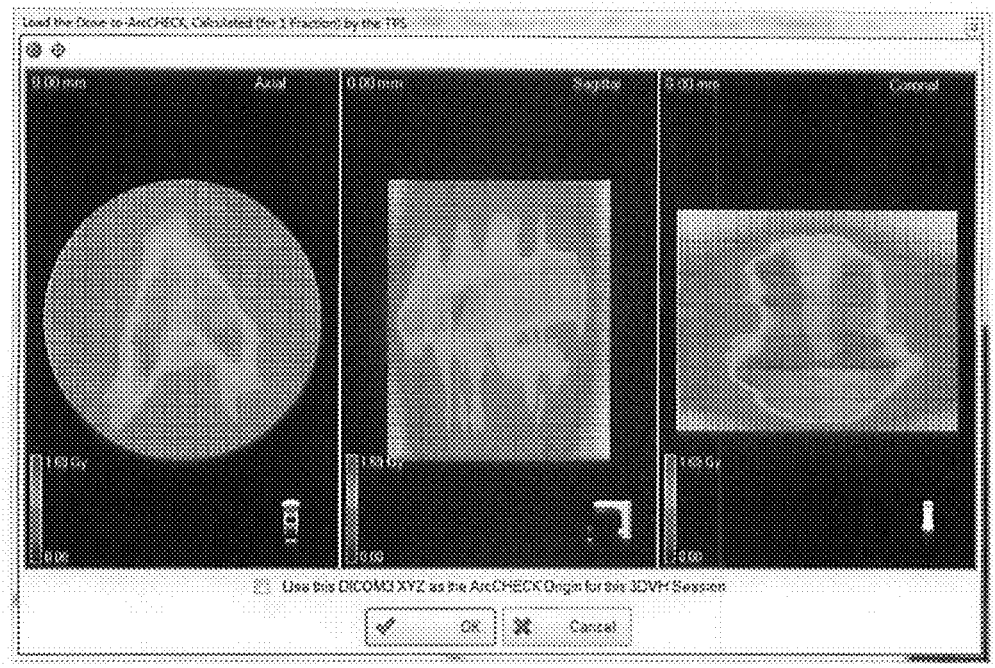

Referring to FIG. 22, after the ACML is loaded and the plan is SYNC'ed, 3DVH prompts the user for the TPS dose-to-AC to be loaded. Here, the TPS dose-to-AC is loaded, but not yet properly aligned. To align TPS the dose-to-AC, the TPS plan-on-AC is loaded in order to extract the isocenter position in the DICOM3 coordinate system, as in FIG. 23. In FIG. 24, the TPS dose-to-AC is shown now properly aligned and ready to be loaded, allowing the AC-PDP calculation to begin.

Figure 25:
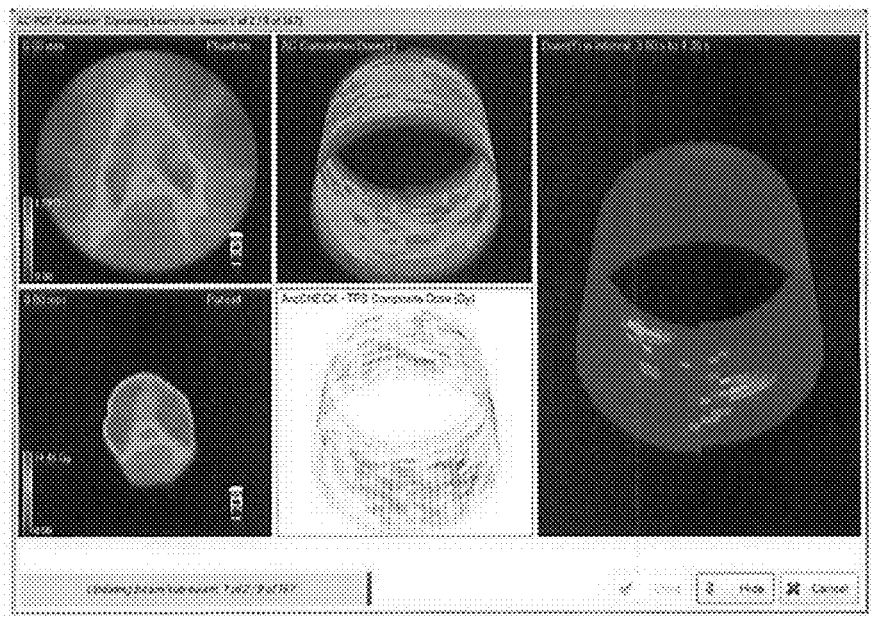
Figure 26:
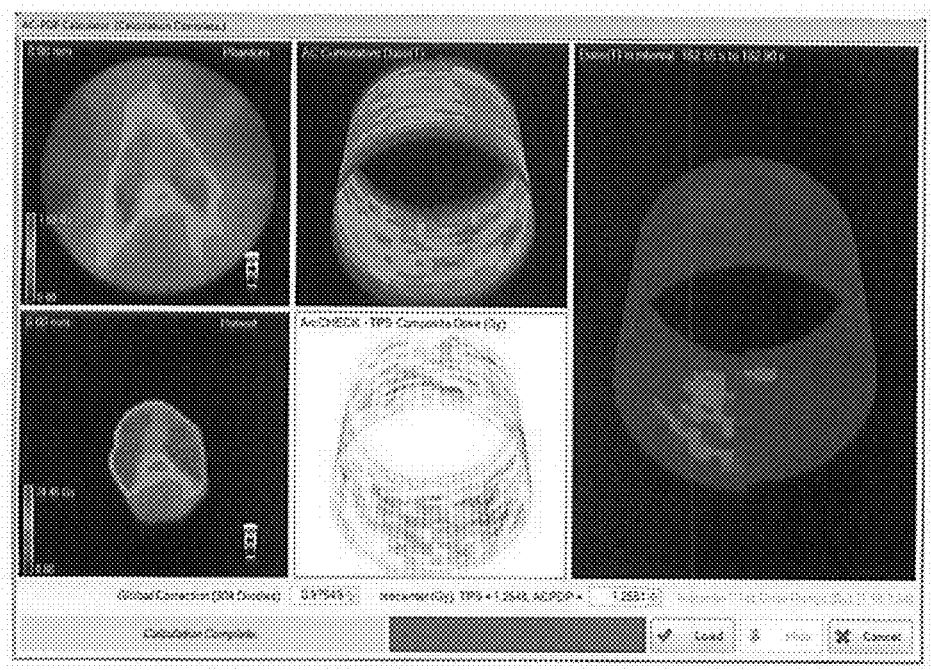

While the AC-PDP calculation takes place, the custom progress monitor will update the sub-beam(T) low density dose as the sub-beams are calculated (each sub-beam calculation consists of both AC-CONV and MORPH-NORM for that sub-beam) (see FIG. 25). After the AC-PDP calculation is complete, the GCF and the phantom isocenter dose (both TPS and MGDR) is displayed. FIG. 26 illustrates an example where the GCF is on the lower range of what is common is shown. This is very rare. The GCF will typically be 0.99-1.01.

Figure 27:
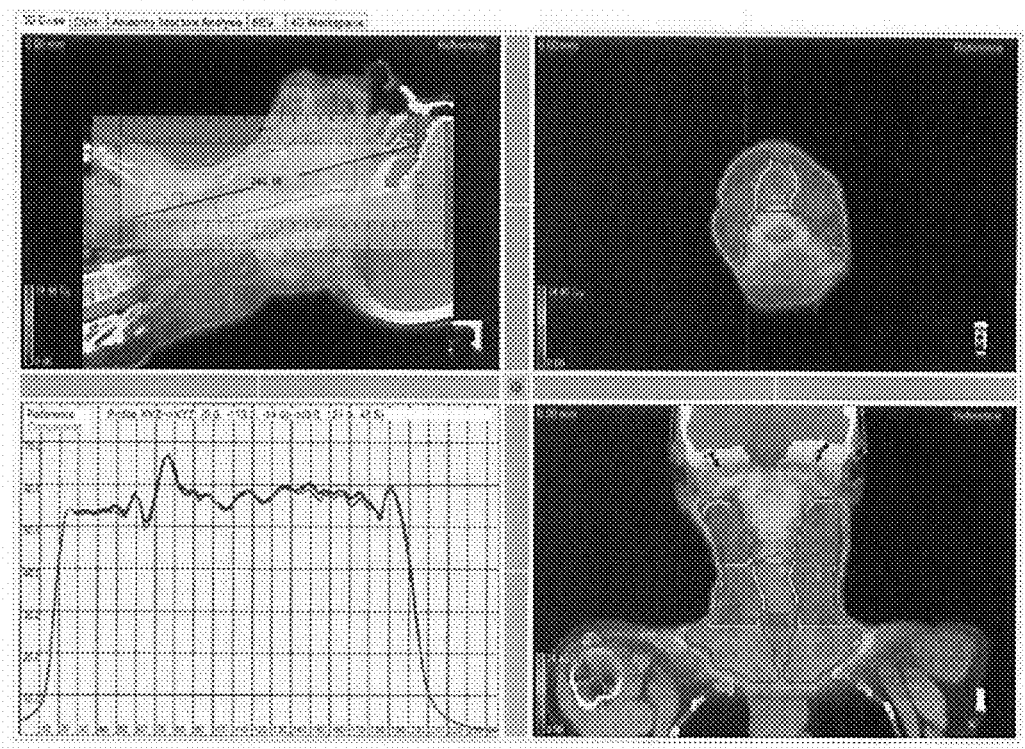
Figure 28:
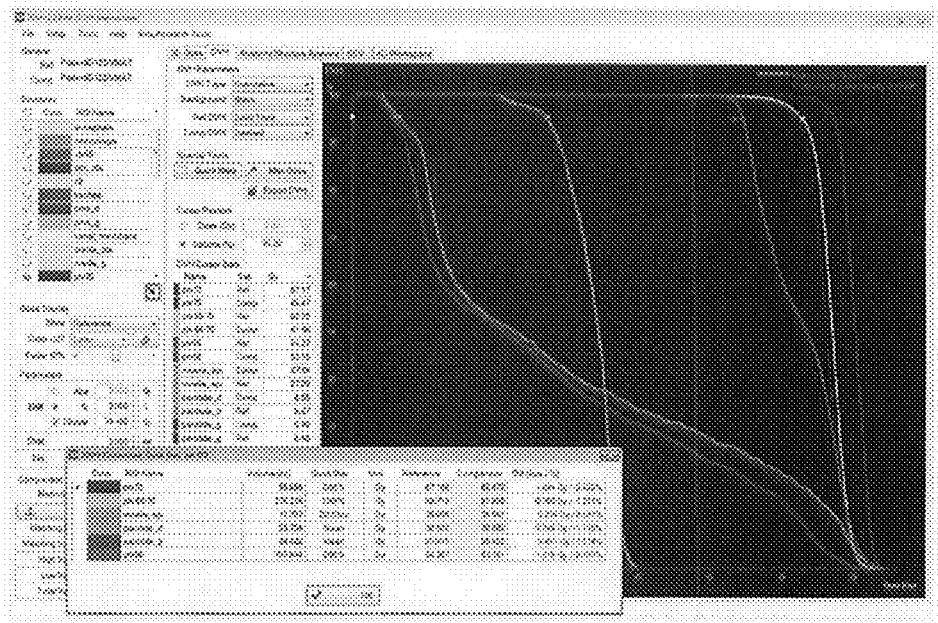
Figure 29:
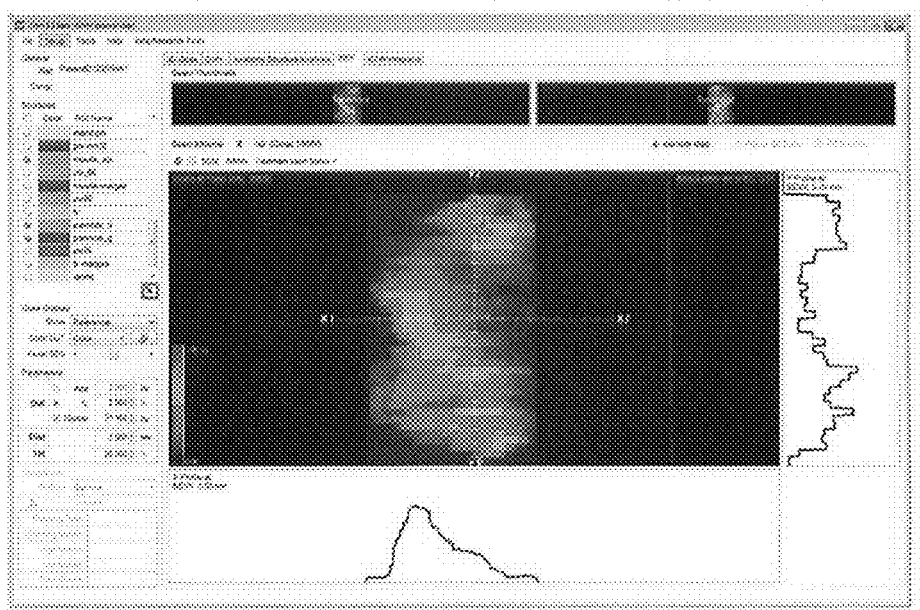
Figure 30:
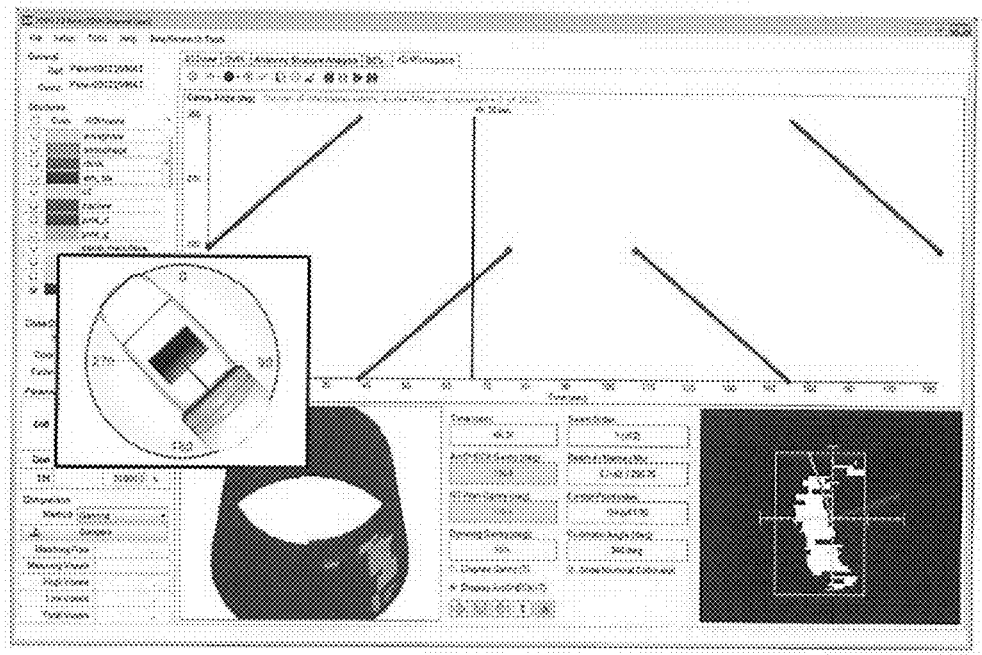

With reference to FIG. 27, after the AC-PDP calculation is complete and loaded, the patient dose can be analyzed in interactive 2D anatomical planes and 1D dose profiles. In FIG. 28, analysis of TPS vs. AC-PDP patient dose using interactive DVH and user-customized "Quick Stats" is seen. The BEV tab for VMAT beams shows integral beam fluence normal to the CAX over all gantry angles of a beam (as in FIG. 29). For AC-PDP analysis, the 4D workspace will show the synchronized RT Plan and interactive 4D tools for analyzing gantry angle, MLC segments, cumulative AC dose, or differential AC dose (as in FIG. 30).

Figure 31:
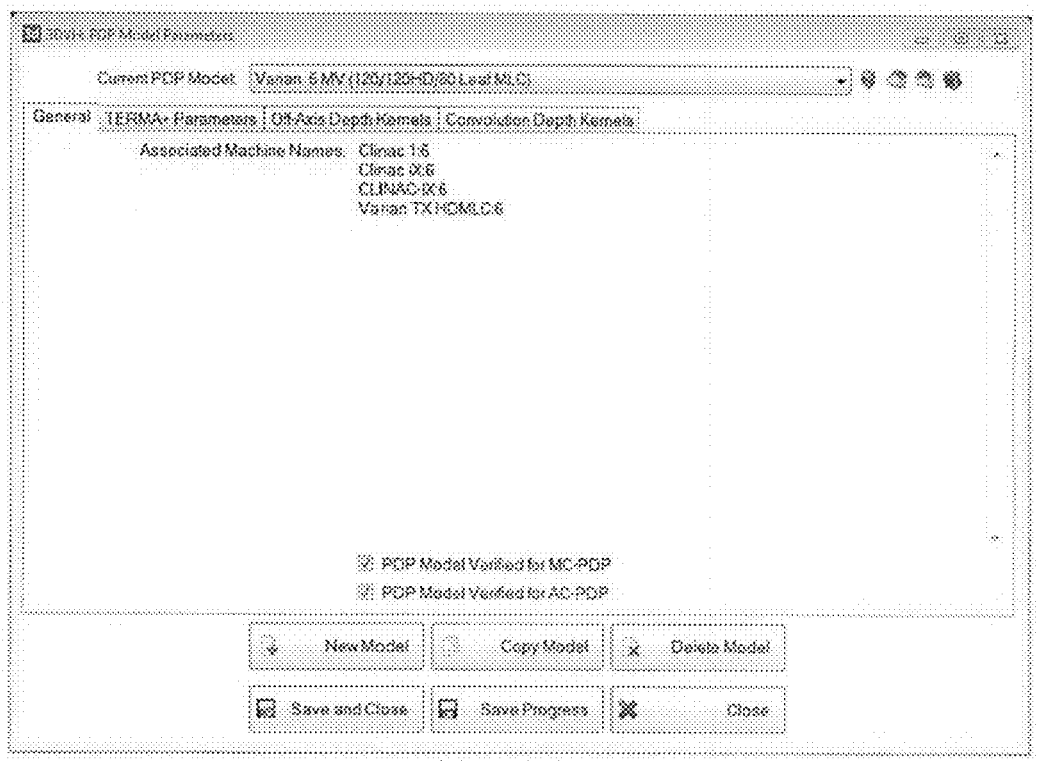
FIGS. 31-36 illustrate PDP model parameters.
Figure 32:
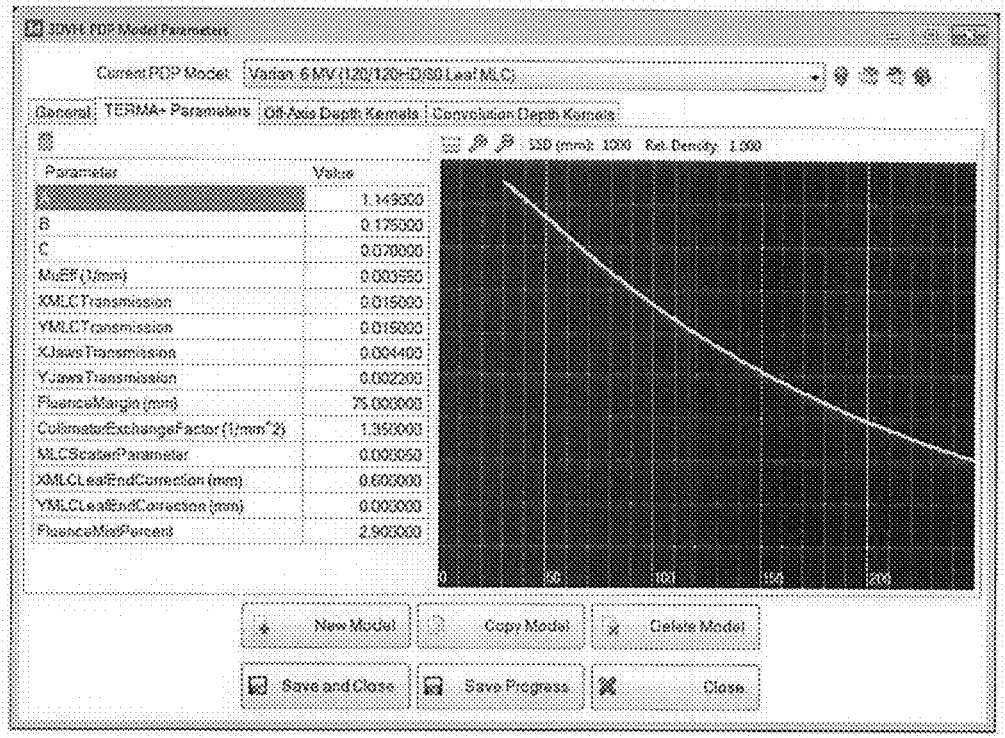
Figure 33:
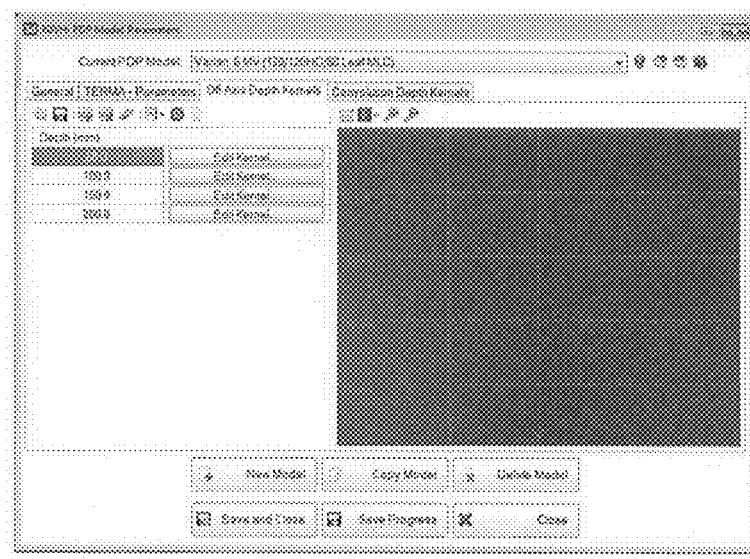
Figure 34:
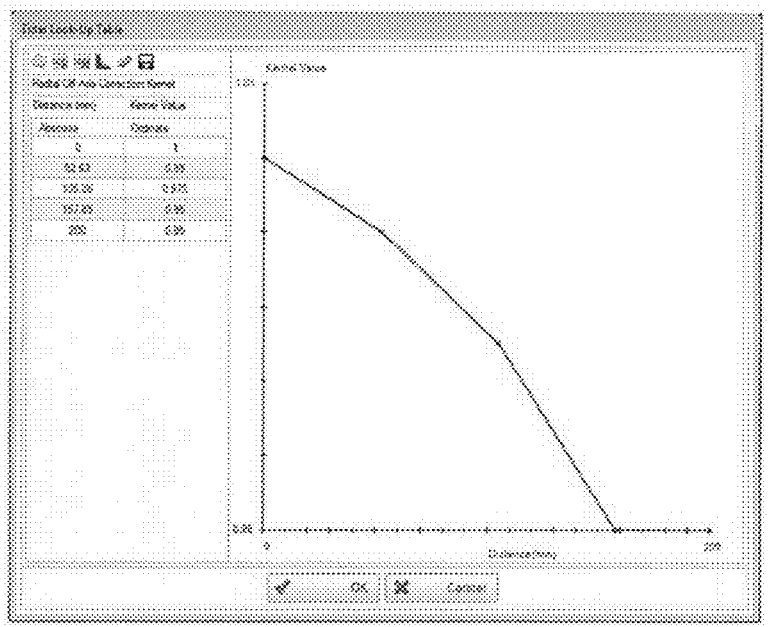
Figure 35:
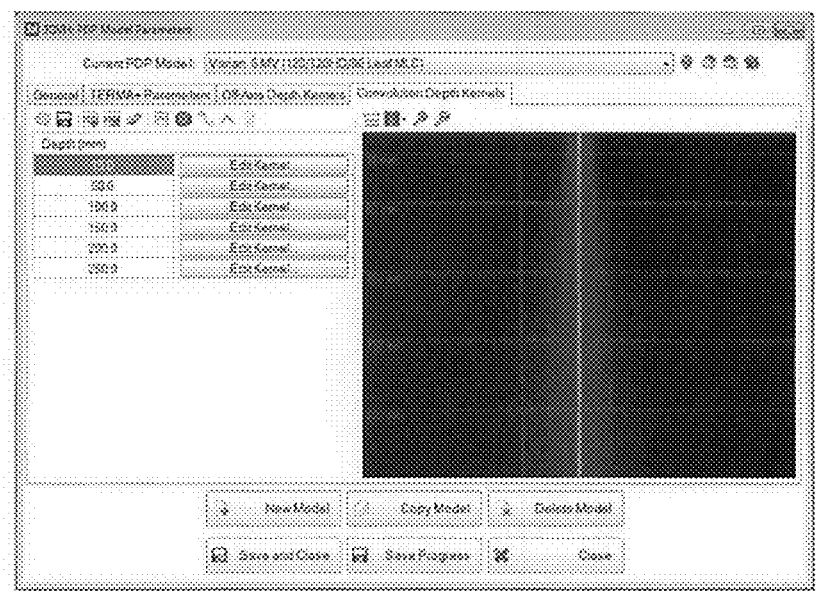
Figure 36:
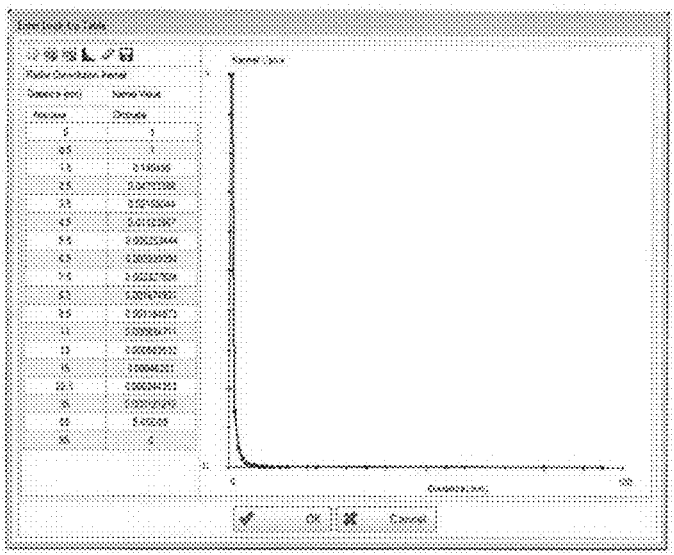
Figure 37:
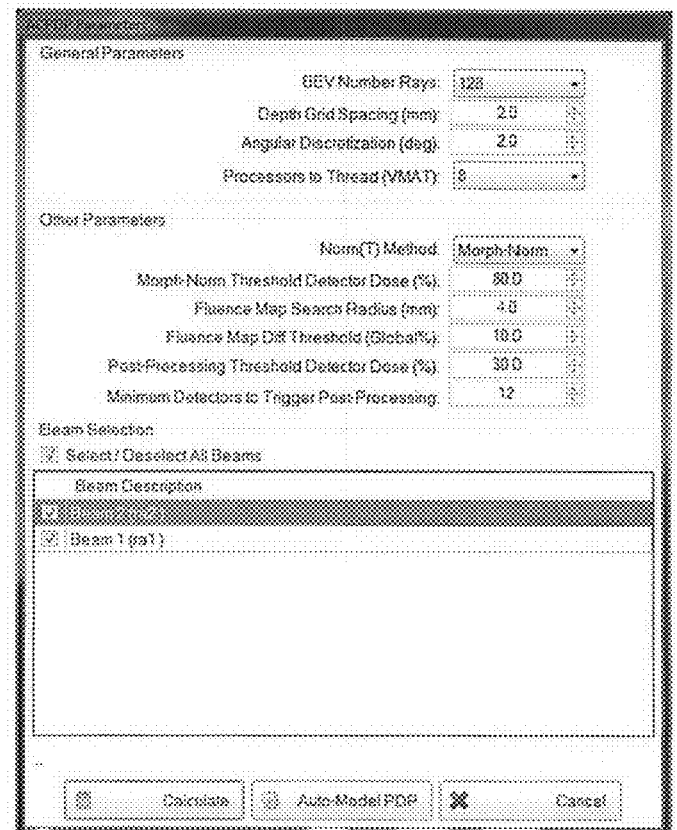
FIGS. 37-40 illustrate advanced/diagnostic tools available in service mode.

Referring to FIG. 31-36, PDP Model parameters will be described. The parameters are viewed and/or edited by a user via the following tabs:

a. FIG. 31—General tab showing the associated machine names and energies;
b. FIG. 32—TERMA+ Parameters tab;
c. FIG. 33—Off-Axis Depth Kernels tab, showing the depths used to define the off-axis kernels (FIG. 34 is an example of an off-axis depth kernel at a distance depth —off axis profiles at shallower depths will increase the farther off-axis the ray);
d. FIG. 35—Convolution Depth Kernels tab, showing the depths used to define the dose deposition kernels (FIG. 36 is an example of convolution radial depth kernel definition);

3DVH has a service mode that allows visibility and access to advanced features that are preferably not provided commercially to the user. Some of the tools are diagnostic in nature, and others designed for research and testing. Examples of these advanced tools are shown in FIGS. 37 through 40. For instance, in FIG. 37 advanced AC-PDP calculation parameter editing can be allowed in service/diagnostic mode, and will appear if activated via the file menu.

Figure 38:
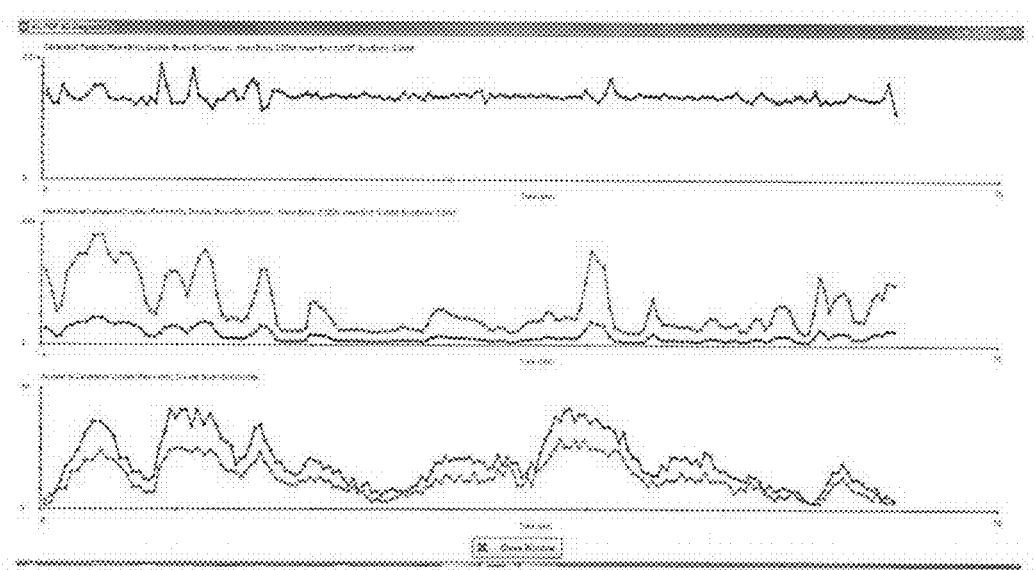

Referring to FIG. 38, AC-PDP 4D diagnostics will appear if in service mode and the option activated via the file menu. These can be used to diagnose problems in the input data or AC-PDP calculation components. The Top Row in FIG. 38 shows MORPH-NORM calibration factors at entry (red) and exit (blue) surfaces. The red and blue curves should be very close to one another, and if not it could signify VI or SYNC errors. The Middle Row shows Max diode doses at entry and exit surfaces, giving some idea of the peak dose per sub-beam. The Bottom Row shows the number of qualifying calibration (MORPH-NORM) diodes at entry and exit surfaces; usually the number of calibration diodes at the exit surface should be larger than the number at the entry surface due to geometric projection of the sub-beam dose pattern.

Figure 39:
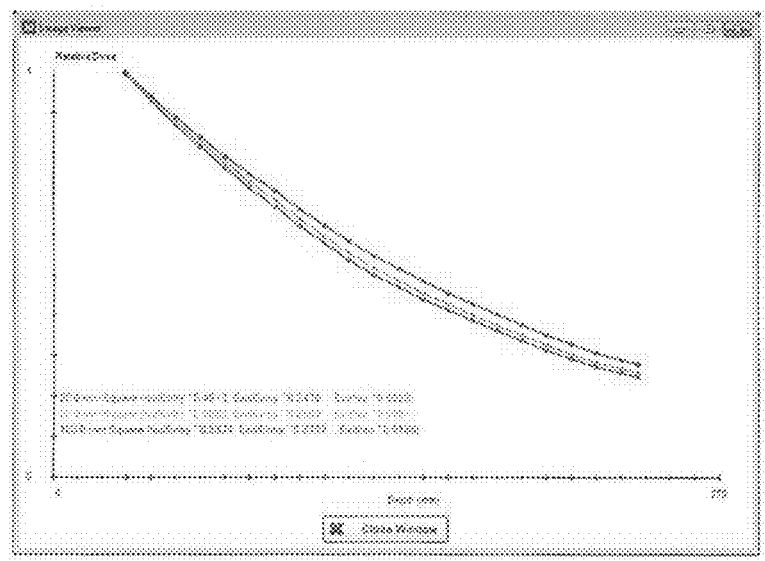
Figure 40:
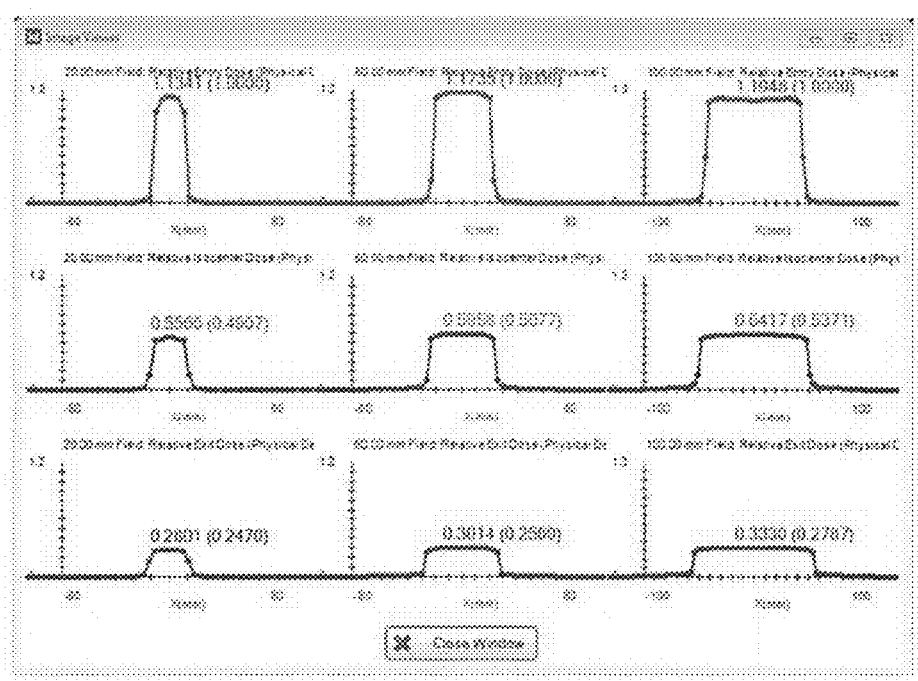

When optimizing AC-PDP parameters, PDDs for user-input field sizes can be quickly calculated and displayed (see FIG. 39). These are driven by all parameters (TERMA+, Off-Axis, and Convolution) but fitting these curves to measurements is most useful when optimizing the convolution depth kernels. When optimizing AC-PDP parameters, dose profiles at entry, isocenter, and exit distances for user-input field sizes can be quickly calculated and displayed (as in FIG. 40). Using isocenter/entry and exit/entry ratios is an important tool when modeling AC-PDP parameters.

In general, the foregoing description is provided for exemplary and illustrative purposes; the present invention is not necessarily limited thereto. Rather, those skilled in the art will appreciate that additional modifications, as well as adaptations for particular circumstances, will fall within the scope of the invention as herein shown and described.

What is claimed is:

1. A method for performing composite dose quality assurance with a three-dimensional (3D) radiation detector array, the method comprising:
   delivering, from a moving radiation source, a radiation fraction to the 3D array according to a radiation treatment (RT) plan;
   measuring absolute dose per detector of the 3D array, per unit of time;
   determining a radiation source emission angle per unit of time;
   synchronizing the RT plan with the measured absolute doses and determined radiation source emission angles to determine an absolute time for a control point of each beam of the synchronized RT plan;
   converting the beams of the synchronized RT plan into a series of sub-beams;
   generating a 3D relative dose grid for each of the sub-beams;
   applying a calibration factor grid to each of the 3D relative dose grids to determine a 3D absolute dose grid for each of the sub-beams;
   summing the 3D absolute dose grids to generate a 3D absolute dose deposited in the 3D array; and
   determining a 3D dose correction grid for application to the RT plan based on the 3D absolute dose.

* * * * *